US012708294B2

(12) United States Patent
Kamada et al.

(10) Patent No.: US 12,708,294 B2
(45) Date of Patent: Aug. 18, 2026

(54) DEVICE AND METHOD FOR ASSESSING STERNAL COMPRESSION

(71) Applicant: HAMAMATSU PHOTONICS K.K., Hamamatsu (JP)

(72) Inventors: Tsuyoshi Kamada, Hamamatsu (JP); Wataru Kamo, Hamamatsu (JP); Hitoshi Kano, Hamamatsu (JP)

(73) Assignee: HAMAMATSU PHOTONICS K.K., Hamamatsu (JP)

( * ) Notice: Subject to any disclaimer, the term of this patent is extended or adjusted under 35 U.S.C. 154(b) by 341 days.

(21) Appl. No.: 18/290,490

(22) PCT Filed: Mar. 23, 2022

(86) PCT No.: PCT/JP2022/013668
§ 371 (c)(1),
(2) Date: Nov. 14, 2023

(87) PCT Pub. No.: WO2022/244459
PCT Pub. Date: Nov. 24, 2022

(65) Prior Publication Data
US 2024/0277264 A1 Aug. 22, 2024

(30) Foreign Application Priority Data
May 18, 2021 (JP) ................................ 2021-084054

(51) Int. Cl.
*A61B 5/1455* (2006.01)
*A61B 5/00* (2006.01)

(52) U.S. Cl.
CPC ........ *A61B 5/14551* (2013.01); *A61B 5/6814* (2013.01); *A61B 5/742* (2013.01)

(58) Field of Classification Search
CPC ... A61B 5/14551; A61B 5/6814; A61B 5/742; A61B 5/0053; A61B 5/4884;
(Continued)

(56) References Cited

U.S. PATENT DOCUMENTS

2017/0258381 A1* 9/2017 Ozaki .................. A61B 5/1455
2018/0020959 A1* 1/2018 Koyama ........... A61B 5/14535 600/328
(Continued)

FOREIGN PATENT DOCUMENTS

EP 3409258 B1 12/2020
JP 2005-046606 A 2/2005
(Continued)

OTHER PUBLICATIONS

Extended European Search Report issued on Apr. 16, 2025 in corresponding European patent application 22804377.4.
(Continued)

*Primary Examiner* — Dmitry Suhol
*Assistant Examiner* — Julie Grace Dosher
(74) *Attorney, Agent, or Firm* — Faegre Drinker Biddle & Reath LLP

(57) ABSTRACT

The evaluation apparatus is an apparatus for evaluating chest compression, and includes a measuring unit, a compression position evaluation unit, and an instruction unit. The measuring unit obtains numerical values relating to temporal changes in a total hemoglobin concentration, an oxygenated hemoglobin concentration, and a deoxygenated hemoglobin concentration of the head. The compression position evaluation unit determines whether compression position on a sternum is appropriate based on a first indicator and a second indicator, the first indicator relating to a temporal change ratio of the oxygenated hemoglobin concentration with respect to the temporal change in the total hemoglobin concentration, and the second indicator relating to a correlation between the temporal change in the oxygenated hemoglobin concentration and the temporal change in the deoxygenated hemoglobin concentration. When the com-
(Continued)

pression position on the sternum is inappropriate, the instruction unit instructs to change the compression position.

16 Claims, 17 Drawing Sheets

(58) Field of Classification Search
CPC .............. A61B 5/14542; A61B 5/0075; A61B 2505/01; A61B 5/4848; A61H 31/005
See application file for complete search history.

(56) References Cited

U.S. PATENT DOCUMENTS

| | | | | |
|---|---|---|---|---|
| 2018/0110667 | A1* | 4/2018 | Freeman | A61G 13/08 |
| 2019/0029919 | A1* | 1/2019 | Suh | A61H 31/006 |
| 2021/0045967 | A1* | 2/2021 | Lampe | A61H 31/007 |
| 2021/0212889 | A1* | 7/2021 | Alsbou | G16H 20/40 |

FOREIGN PATENT DOCUMENTS

| | | | |
|---|---|---|---|
| JP | 2012-223451 | A | 11/2012 |
| JP | 2013-169280 | A | 9/2013 |
| JP | 2018-042715 | A | 3/2018 |
| KR | 20170090993 | A | 8/2017 |

OTHER PUBLICATIONS

International Preliminary Report on Patentability mailed Nov. 30, 2023 for PCT/JP2022/013668.

* cited by examiner

*Fig.5*
(a)
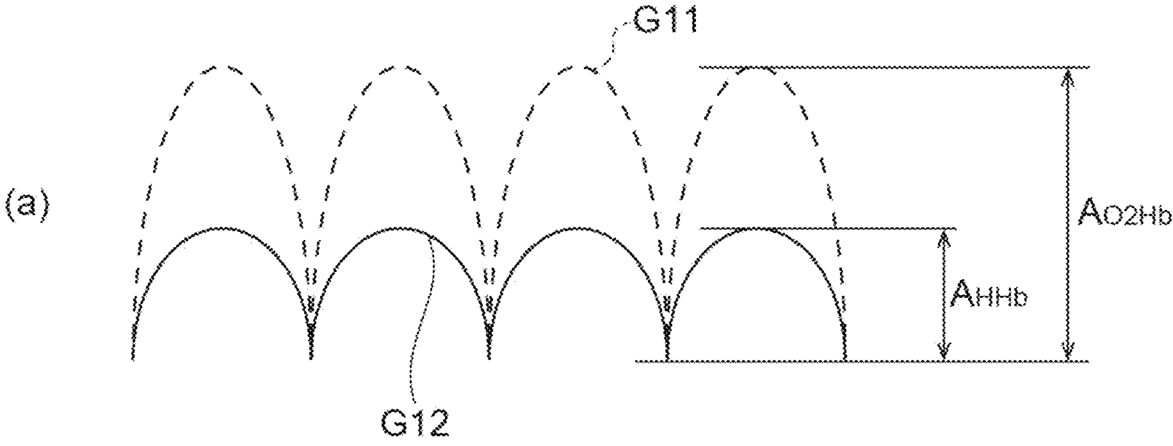
(b)
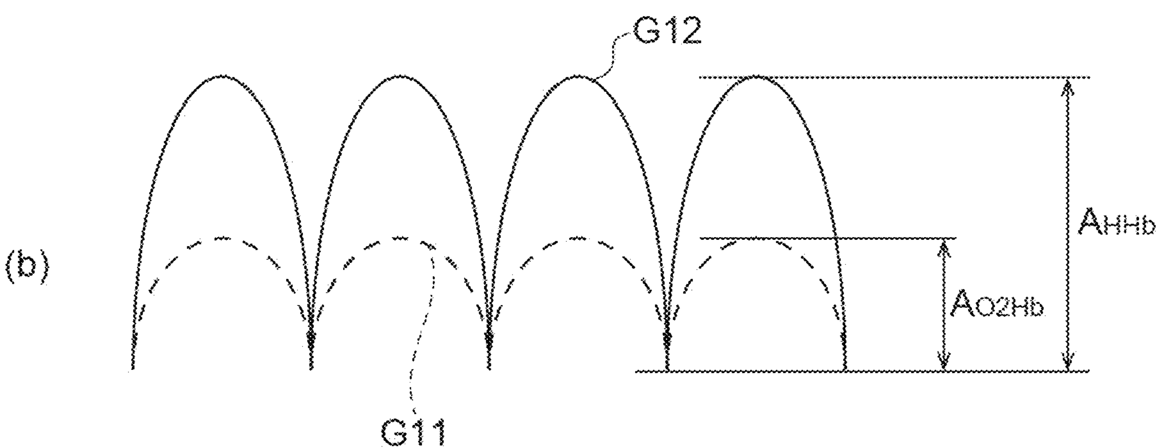

*Fig.6*
(a)
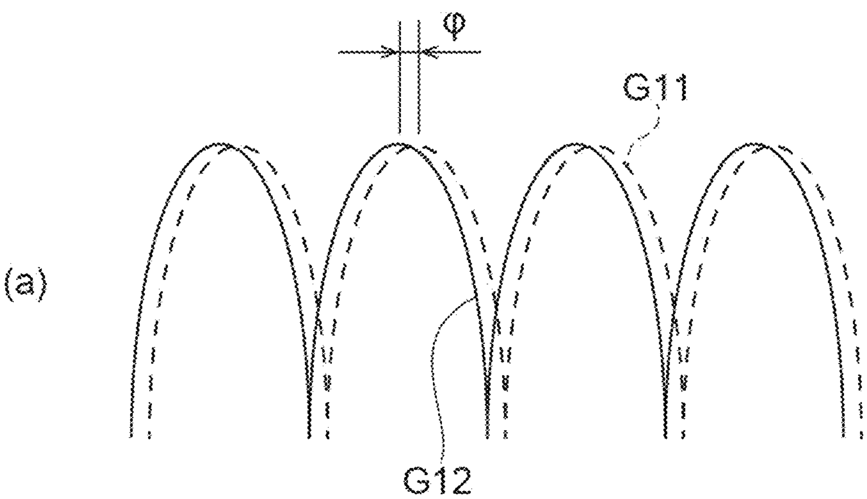
(b)
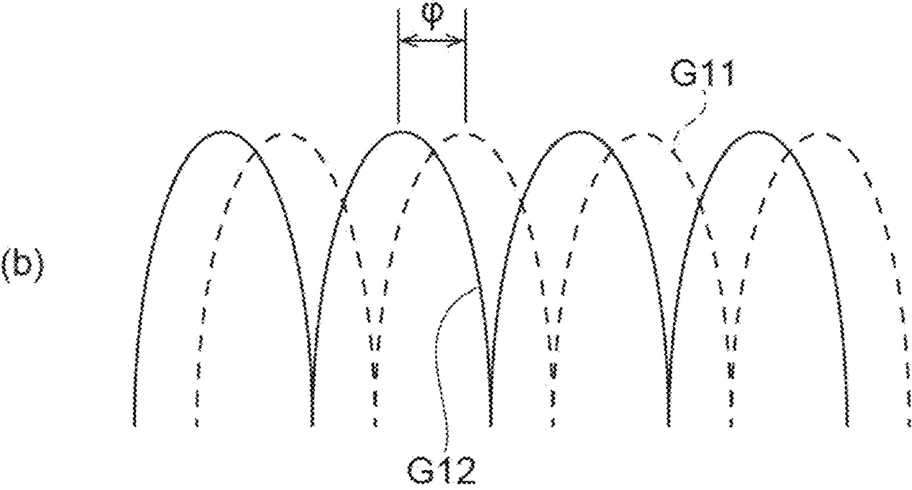

*Fig.8*
(a)
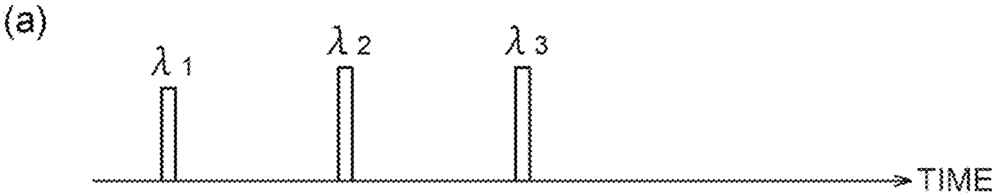
(b)
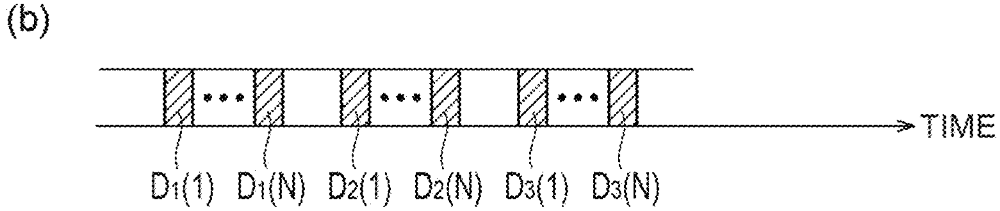

(μ Mol)
4
3
2
1
0
-1
-2
150
160
170
180
190
200
210
G21
G22
G23
TIME (SECONDS)

(μ mol/l)
3
2
1
0
-1
-2
-3
100
200
300
400
500
TIME (SECONDS)
G31
G32
G33
G34

(a)
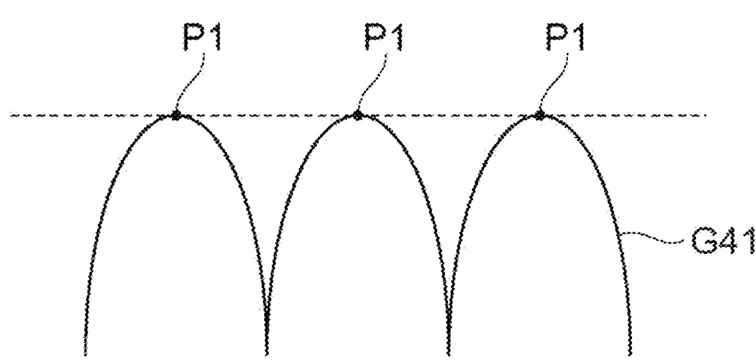
(b)
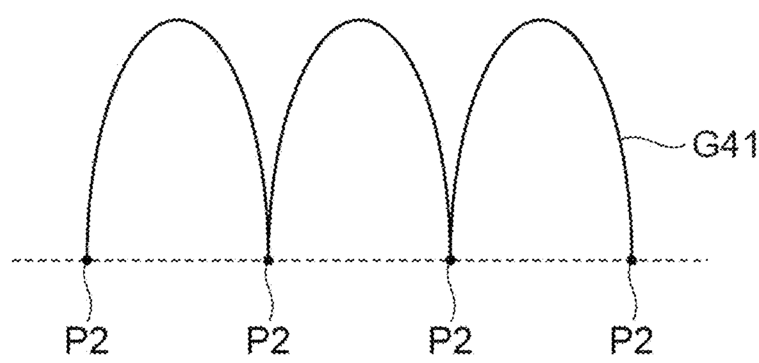

(a)
(b)
1.00
0.00
-1.00
80.0
50.0
20.0
A
B
A
A
B
A
B
C
C
E1
C
D
E2
C
D
C
E3
E4
C
D
C
10:03
10:04
10:05
10:06
10:07
10:08
10:09
10:10
10:11
10:12
10:13
10:14
10:15
10:16
10:17
10:18
TIME (HOURS:MINUITES)

DEVICE AND METHOD FOR ASSESSING STERNAL COMPRESSION

TECHNICAL FIELD

The present disclosure relates to an evaluation apparatus and evaluation method for chest compression.

BACKGROUND ART

Patent Literature 1 discloses a device for assisting a rescuer when performing cardio pulmonary resuscitation (CPR) on a cardiorespiratory arrest person. This apparatus comprises at least one of a pulse sensor for measuring the heart rate of the cardiorespiratory arrest person and a SpO2 for measuring blood oxygen, electronics for processing the output of the sensor and determining one or more actions to be taken by a rescuer to improve current CPRs, and a reminder device that transmits one or more actions to the rescuer.

CITATION LIST

Patent Literature

Patent Literature 1: Japanese Unexamined Patent Publication No. 2005-46606

SUMMARY OF INVENTION

Technical Problem

In cardiopulmonary resuscitation, chest compression is performed in combination with an artificial respiration. The chest compression is an action of giving artificial pulsation to a stopped heart by periodically compressing the lower half of the sternum with the hand of another person. The primary purpose of chest compression is to supply blood oxygen to the brain of a cardiorespiratory arrest person. Whether the chest compression is appropriately performed greatly affects the success rate of cardiopulmonary resuscitation. Therefore, there is a need for a useful method and apparatus for objectively evaluating whether the chest compression is being properly performed.

An object of the present disclosure is to provide an apparatus and a method capable of increasing a success rate of cardiopulmonary resuscitation by evaluating whether the chest compression is appropriately performed and notifying the rescuer of the fact that the chest compression is inappropriate in a case where the chest compression is not appropriately performed.

Solution to Problem

An evaluation apparatus according to the present disclosure is an apparatus for evaluating chest compression, and includes a measuring unit, a compression position evaluation unit, and an instruction unit. The measuring unit obtains numerical values relating to temporal changes in a total hemoglobin concentration, an oxygenated hemoglobin concentration, and a deoxygenated hemoglobin concentration in a head, which vary due to repetition of the chest compression. The compression position evaluation unit calculates a first indicator and a second indicator based on the numerical values. The first indicator is relating to a temporal change ratio of one or both of the oxygenated hemoglobin concentration and the deoxygenated hemoglobin concentration with respect to a temporal change in the total hemoglobin concentration. The second indicator is relating to a correlation between a temporal change in the oxygenated hemoglobin concentration and a temporal change in the deoxygenated hemoglobin concentration. The compression position evaluation unit determines whether a compression position on the sternum is appropriate based on the first indicator and the second indicator. The instruction unit instructs to change the compression position in a case where the compression position on the sternum is inappropriate.

An evaluation method according to the present disclosure is a method for evaluating chest compression, and includes: a step of obtaining numerical values relating to temporal changes in a total hemoglobin concentration, an oxygenated hemoglobin concentration, and a deoxygenated hemoglobin concentration of a head, which vary due to repetition of the chest compression; a step of calculating a first indicator and a second indicator based on the numerical values, the first indicator relating to a temporal change ratio of one or both of the oxygenated hemoglobin concentration and the deoxygenated hemoglobin concentration with respect to a temporal change in the total hemoglobin concentration, and the second indicator relating to a correlation between a temporal change in the oxygenated hemoglobin concentration and a temporal change in the deoxygenated hemoglobin concentration; a step of determining whether a compression position on a sternum is appropriate based on the first indicator and the second indicator; and a step of instructing to change the compression position in a case where the compression position on the sternum is inappropriate.

Advantageous Effects of Invention

According to the apparatus and the method of the present disclosure, it is possible to increase a success rate of cardiopulmonary resuscitation by evaluating whether the chest compression is appropriately performed and notifying the rescuer of the fact that the chest compression is inappropriate in a case where the chest compression is not appropriately performed.

BRIEF DESCRIPTION OF DRAWINGS

FIG. 5 is a diagram conceptually showing temporal changes from initial amounts in an $O_2Hb$ concentration and a HHb concentration. Part (a) of FIG. 5 shows a case where an amplitude $A_{O2Hb}$ of the temporal change from the initial amount of the $O_2Hb$ concentration is higher than an amplitude $A_{HHb}$ of the temporal change from the initial amount of the HHb concentration. Conversely, Part (b) of FIG. 5 shows a case where the amplitude $A_{HHb}$ is higher than the amplitude $A_{O2Hb}$.

FIG. 6 is a diagram conceptually showing temporal changes from initial amounts in the $O_2Hb$ concentration and the HHb concentration. Part (a) of FIG. 6 shows a case where an absolute value of a phase difference $\varphi$ between the temporal change from the initial amount of the $O_2Hb$ concentration and the temporal change from the initial amount of the HHb concentration are low. Part (b) of FIG. 6 shows a case where the absolute value of the phase difference φ is high.

Part (a) of FIG. 8 is a diagram illustrating incident timings of measurement lights having wavelengths $\lambda_1$ to $\lambda_3$. Part (b) of FIG. 8 is a diagram illustrating output timings of digital signals from an A/D conversion circuit.

Figure 9:
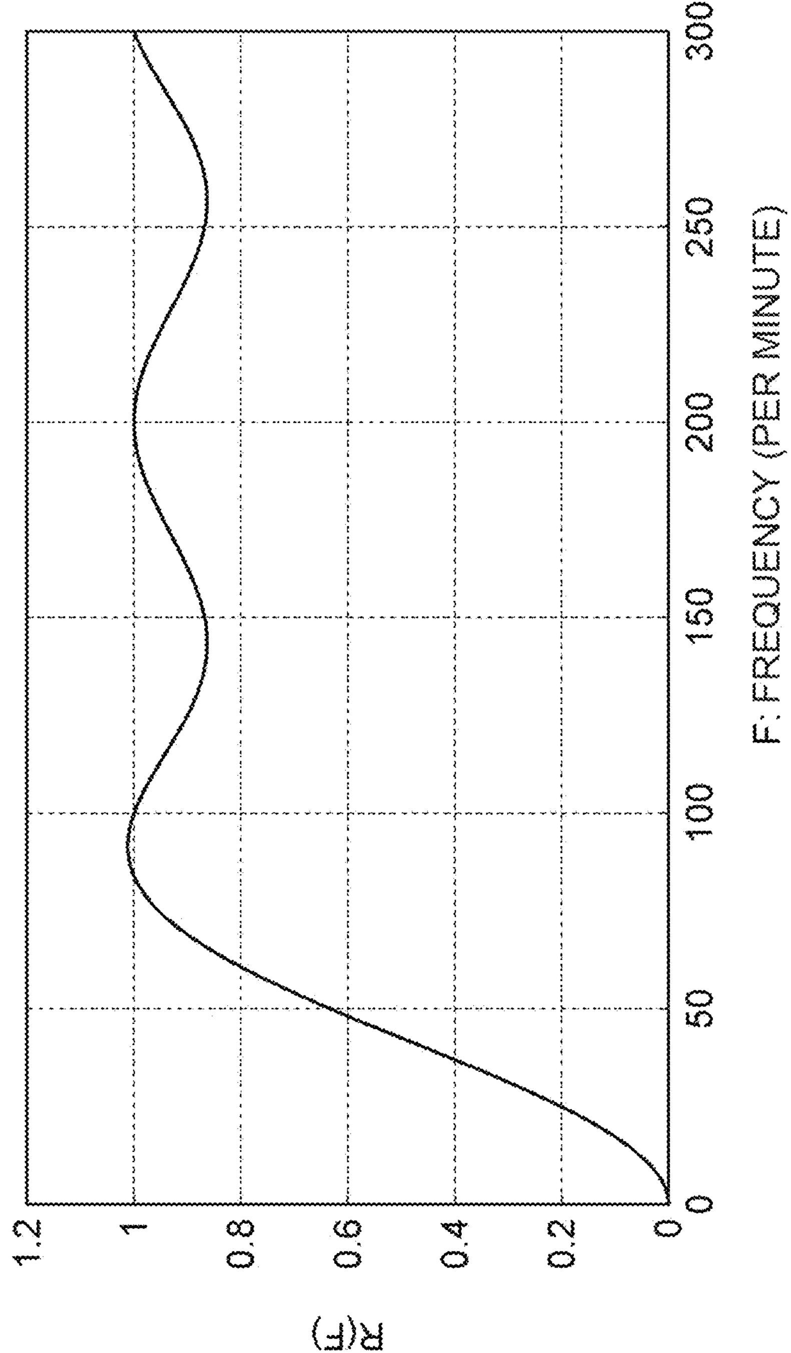

FIG. 9 is a graph showing a filter characteristics of a digital filter.

Figure 10:
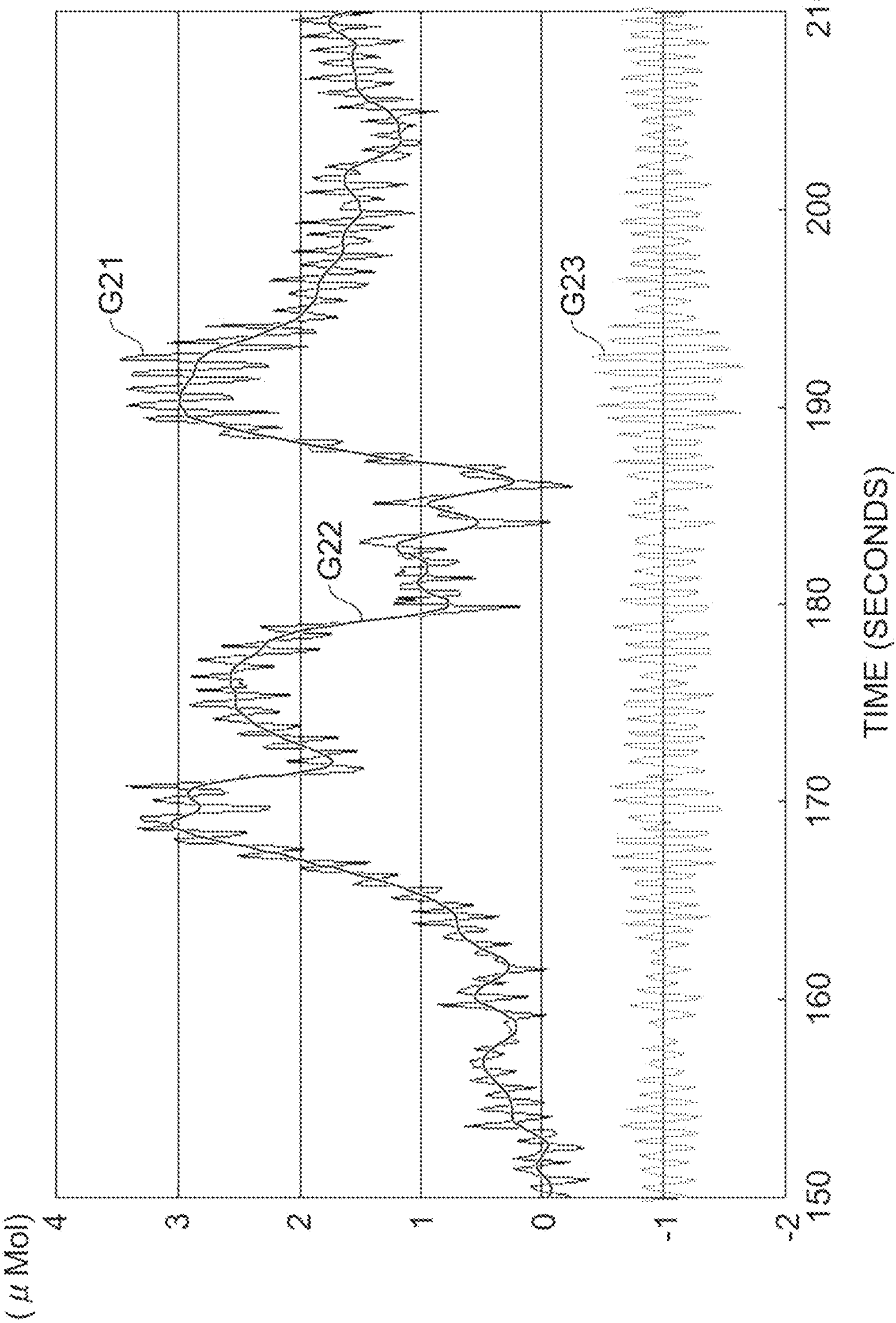

FIG. 10 is a graph showing a result of extracting a temporal variation component caused by a spontaneous heart beat simulating the repetition of the chest compression by removing (or reducing) a frequency component less than a predetermined frequency from frequency components included in a temporal relative change amount of the $O_2Hb$ using the digital filter shown in FIG. 9.

Figure 11:
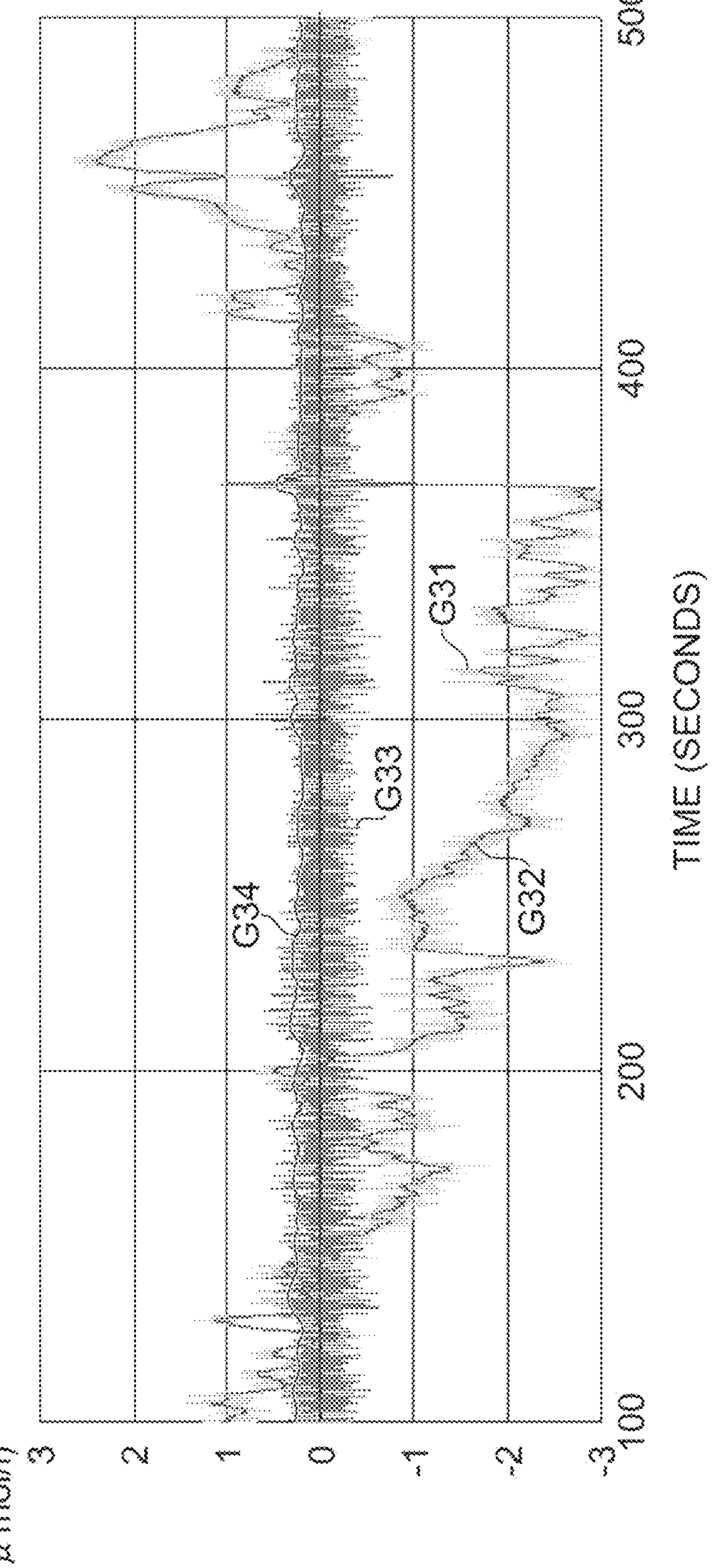

FIG. 11 is a graph showing a result of extracting a temporal variation component caused by the spontaneous heart beat simulating repetition of the chest compression by removing (or reducing) a frequency component less than a predetermined frequency from frequency components included in a temporal relative change amount of a cHb using filtering process.

Part (a) and part (b) of FIG. 12 are diagrams for explaining a concept of a filtering process.

Figure 13:
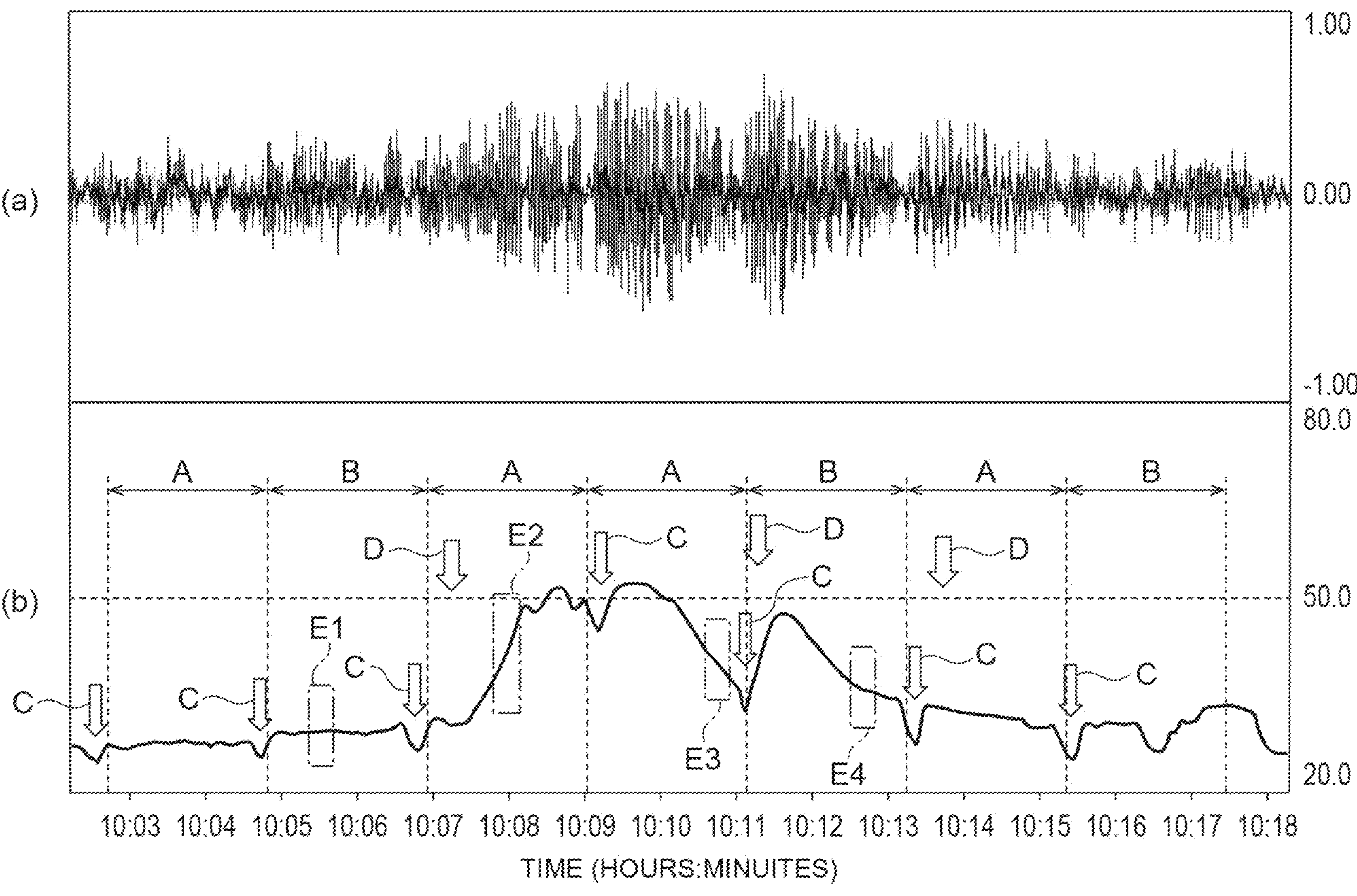

Part (a) of FIG. 13 is a graph showing a temporal change in a cHb concentration of a head in cardiopulmonary resuscitation. Part (b) of FIG. 13 is a graph showing a temporal change in a TOI of the head in cardiopulmonary resuscitation.

Figure 14:
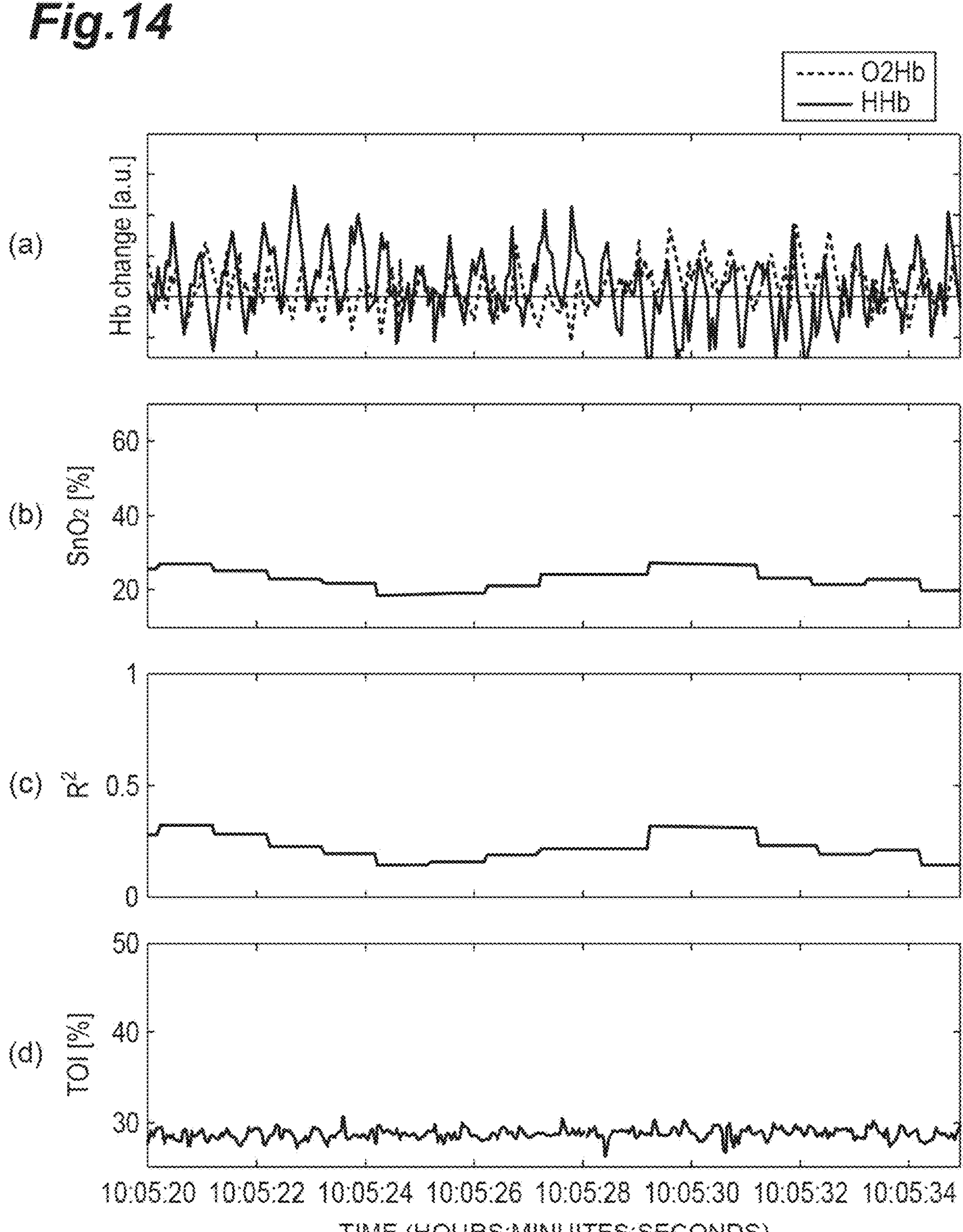

FIG. 14 is a graph showing (a) change amounts of the $O_2Hb$ concentration and the HHb concentration, (b) pulse wave oxygen saturation, (c) a value relating to a phase difference between an $O_2Hb$ pulse wave component and a HHb pulse wave component, and (d) tissue oxygen saturation, in part E1 of FIG. 13.

Figure 15:
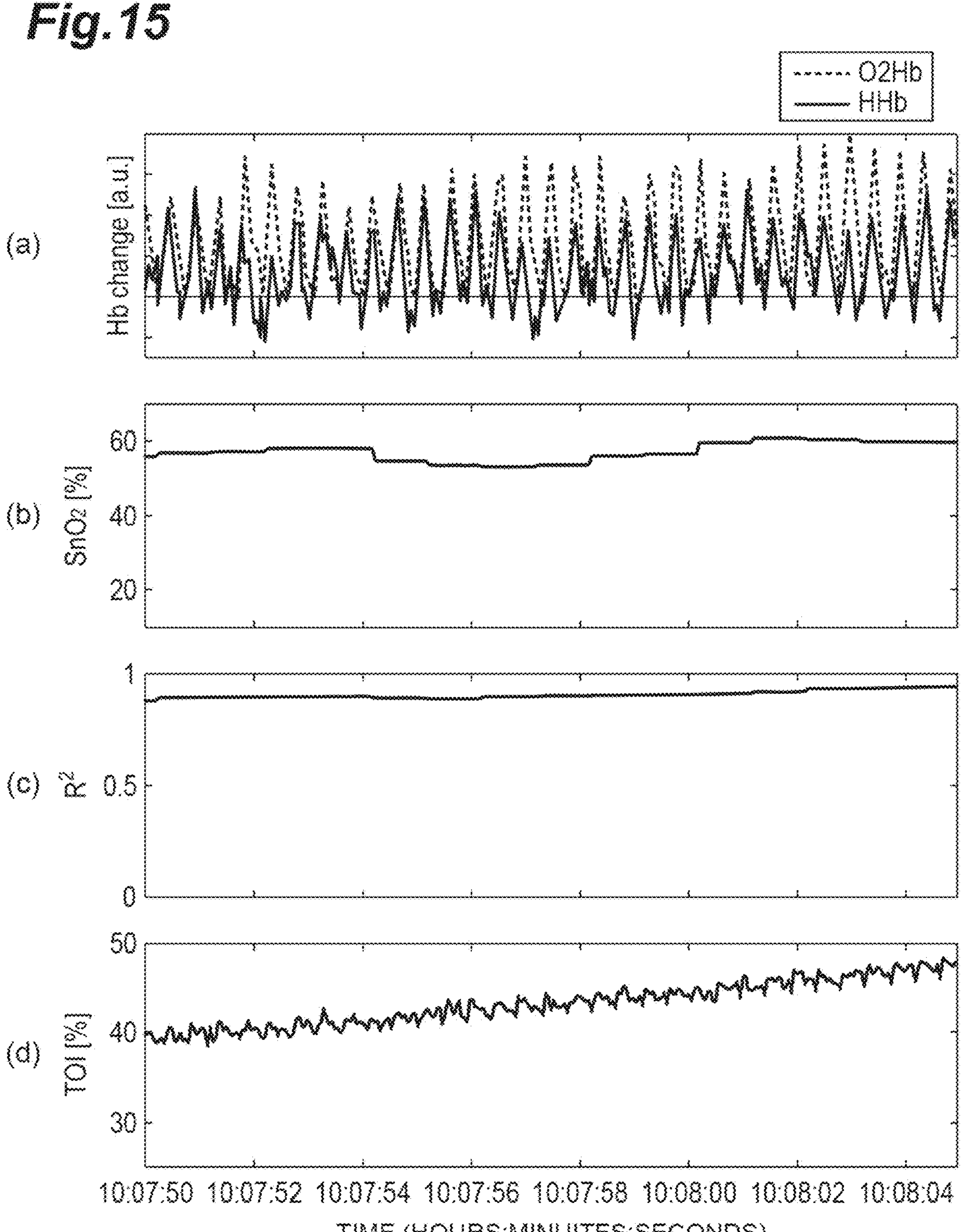

FIG. 15 is a graph showing (a) change amounts of the $O_2Hb$ concentration and the HHb concentration, (b) pulse wave oxygen saturation, (c) a value relating to a phase difference between an $O_2Hb$ pulse wave component and a HHb pulse wave component, and (d) tissue oxygen saturation, in part E2 of FIG. 13.

Figure 16:
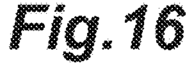

FIG. 16 is a graph showing (a) change amounts of the $O_2Hb$ concentration and the HHb concentration, (b) pulse wave oxygen saturation, (c) a value relating to a phase difference between an $O_2Hb$ pulse wave component and a HHb pulse wave component, and (d) tissue oxygen saturation, in part E3 of FIG. 13.

Figure 17:
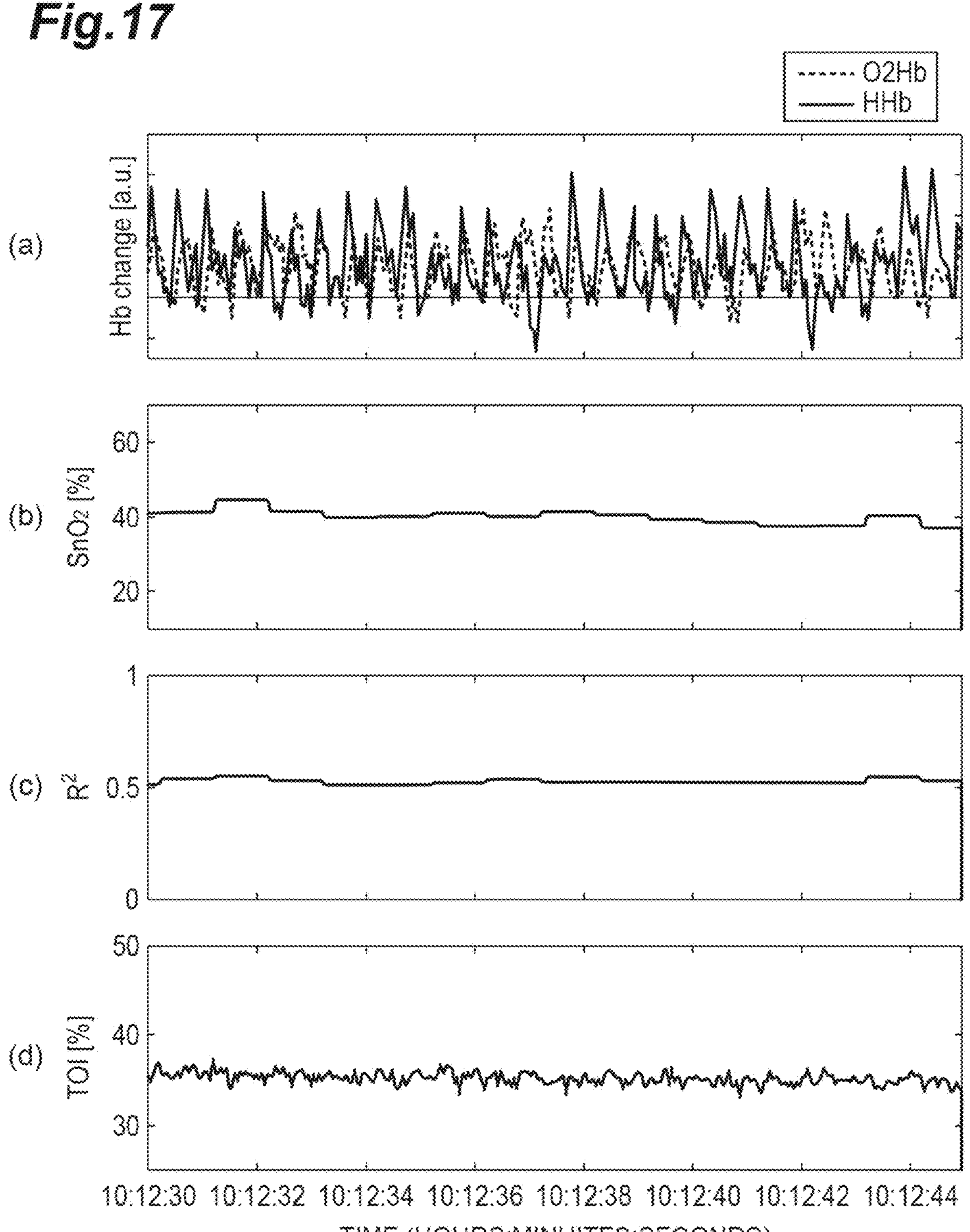

FIG. 17 is a graph showing (a) change amounts of the $O_2Hb$ concentration and the HHb concentration, (b) pulse wave oxygen saturation, (c) a value relating to a phase difference between an $O_2Hb$ pulse wave component and a HHb pulse wave component, and (d) tissue oxygen saturation, in part E4 of FIG. 13.

DESCRIPTION OF EMBODIMENTS

An evaluation apparatus according to the present disclosure is an apparatus for evaluating chest compression, and includes a measuring unit, a compression position evaluation unit, and an instruction unit. The measuring unit obtains numerical values relating to temporal changes in a total hemoglobin concentration, an oxygenated hemoglobin concentration, and a deoxygenated hemoglobin concentration in a head, which vary due to repetition of the chest compression. The compression position evaluation unit calculates a first indicator and a second indicator based on the numerical values and determines whether a compression position on the sternum is appropriate based on the first indicator and the second indicator, the first indicator relating to a temporal change ratio of one or both of the oxygenated hemoglobin concentration and the deoxygenated hemoglobin concentration with respect to a temporal change in the total hemoglobin concentration, and the second indicator relating to a correlation between a temporal change in the oxygenated hemoglobin concentration and a temporal change in the deoxygenated hemoglobin concentration. The instruction unit instructs to change the compression position in a case where the compression position on the sternum is inappropriate.

An evaluation method according to the present disclosure is a method for evaluating chest compression, and includes: a step of obtaining numerical values relating to temporal changes in a total hemoglobin concentration, an oxygenated hemoglobin concentration, and a deoxygenated hemoglobin concentration of a head, which vary due to repetition of the chest compression; a step of calculating a first indicator and a second indicator based on the numerical values and determining whether a compression position on a sternum is appropriate based on the first indicator and the second indicator, the first indicator relating to a temporal change ratio of one or both of the oxygenated hemoglobin concentration and the deoxygenated hemoglobin concentration with respect to a temporal change in the total hemoglobin concentration, and the second indicator relating to a correlation between a temporal change in the oxygenated hemoglobin concentration and a temporal change in the deoxygenated hemoglobin concentration; and a step of instructing to change the compression position in a case where the compression position on the sternum is inappropriate.

During cardiopulmonary resuscitation, at least two rescuers may alternately perform the chest compression in order to continuously continue the chest compression for a long time. And when the rescuer changes, a compression position on a sternum naturally changes slightly. The present inventors observed temporal changes in tissue oxygenation index (TOI), oxygen saturation in a pulse wave component ($SnO_2$), $R^2$, the oxygenated hemoglobin concentration, and the deoxygenated hemoglobin concentration in a head undergoing the chest compression. During that time, the rescuer was changed multiple times. As a result, it was found that $SnO_2$, $R^2$, the ratio of an amplitude of the temporal change in the total hemoglobin concentration to an amplitude of the temporal change in the oxygenated hemoglobin concentration, the ratio of an amplitude of the temporal change in the total hemoglobin concentration to an amplitude of the temporal change in the deoxygenated hemoglobin concentration (hereinafter, these are simply referred to as "amplitude ratio"), and a difference between a phase of the temporal change in the oxygenated hemoglobin concentration and a phase of the temporal change in the deoxygenated hemoglobin concentration (hereinafter simply referred to as "phase difference") varies depending on the compression position on the sternum. Further, the present inventors have found that $SnO_2$ and the amplitude ratio indicate a ratio of the temporal change in the oxygenated hemoglobin concentration or the deoxygenated hemoglobin concentration to the temporal change in the total hemoglobin concentration, and $R^2$ and the phase difference indicate a correlation between the temporal change in the oxygenated hemoglobin concentration and the temporal change in the deoxygenated hemoglobin concentration. The present inventors have also found that there is a significant correlation between the temporal change ratio of the oxygenated hemoglobin concentration or the deoxygenated hemoglobin concentration to the temporal change in the total hemoglobin concentration and a tendency (ascending tendency, descending tendency, or leveling off tendency) of a temporal change in TOI of the head, and between the tendency of the temporal change in TOI of the head and the correlation between the temporal change in the oxygenated hemoglobin concentration and the temporal change in the deoxygenated hemoglobin concentration.

In the above-described evaluation method and evaluation apparatus, the first indicator relating to the temporal change ratio of the oxygenated hemoglobin concentration or the deoxygenated hemoglobin concentration with respect to the temporal change in the total hemoglobin concentration and the second indicator relating to the correlation between the temporal change in the oxygenated hemoglobin concentration and the temporal change in the deoxygenated hemoglobin concentration are calculated. Based on the first indicator and the second indicator, it is determined whether the compression position on the sternum is appropriate, that is, whether the tendency of the temporal change in TOI of the head is an ascending tendency or a descending tendency or a leveling off tendency. In a case where the compression position on the sternum is inappropriate, an instruction to change the compression position is given. As described above, by evaluating whether the compression position on the sternum is appropriate and notifying the rescuer of the inappropriateness in a case where the compression position is inappropriate, it is possible to bring the tendency of the temporal change in TOI of the head close to the ascending tendency and to increase the success rate of cardiopulmonary resuscitation.

The measuring unit may include: a light incidence portion that makes the measurement light incident on the head; a light detection portion that detects the measurement light having propagated through the head and generates a detection signal corresponding to an intensity of the measurement light; and a calculation portion that calculates the numerical values based on the detection signal. The step of obtaining may include: a step of making measurement light incident on the head; a step of detecting the measurement light having propagated through the head and generating a detection signal corresponding to an intensity of the measurement light; and a step of calculating the numerical values based on the detection signal. In these cases, temporal changes in the total hemoglobin concentration, the oxygenated hemoglobin concentration, and the deoxygenated hemoglobin concentration of the head can be measured non-invasively and simply. Therefore, it is possible to easily measure the temporal changes in the total hemoglobin concentration, the oxygenated hemoglobin concentration, and the deoxygenated hemoglobin concentration of the head while performing the chest compression.

The compression position evaluation unit or the step of calculating may perform first linear regression based on the numerical values by using a numerical value relating to a pulse wave component of the total hemoglobin concentration as an explanatory variable and a numerical value relating to a pulse wave component of the oxygenated hemoglobin concentration as an objective variable, and may use a regression coefficient value ($SnO_2$) obtained by the first linear regression as the first indicator. The compression position evaluation unit or the step of calculating may perform second linear regression, based on the numerical values described above, between the numerical value relating to the pulse wave component of the oxygenated hemoglobin concentration and a numerical value relating to the pulse wave component of the deoxygenated hemoglobin concentration, and use a determination coefficient value ($R^2$) obtained by the second linear regression as the second indicator. For example, by performing evaluation based on $SnO_2$ and $R^2$ in this manner, it is possible to easily evaluate whether the compression position on the sternum is appropriate.

The compression position evaluation unit or the step of calculating may perform the first linear regression and the second linear regression based on the numerical values obtained during a period from a time of calculation of the first linear regression and the second linear regression to at least 5 seconds before the time of calculation. Considering that the chest compression is recommended to be performed 100 times per minute, the determination accuracy can be improved by securing 5 seconds or more for obtaining the numerical values.

The compression position evaluation unit or the step of determining may determine that the compression position on the sternum is inappropriate when the regression coefficient value ($SnO_2$) served as the first indicator is less than a first threshold value and the determination coefficient value ($R^2$) served as the second indicator is less than a second threshold value. In the case where the value of $SnO_2$ is less than a predetermined threshold value, the deoxygenated hemoglobin concentration is dominant over the oxygenated hemoglobin concentration. In the case where $R^2$ is low, there is no correlation between the change in oxygenated hemoglobin concentration and the change in deoxygenated hemoglobin concentration. Therefore, it is possible to easily evaluate that the compression position on the sternum is inappropriate.

The first threshold value may be 0.5 or more and 1.0 or less. For example, in this case, it is possible to more accurately evaluate whether the compression position on the sternum is appropriate.

The second threshold value may be 0 or more and 0.7 or less. For example, in this case, it is possible to more accurately evaluate whether the compression position on the sternum is appropriate.

The compression position evaluation unit or the step of calculating may calculate a ratio, based on the numerical values, between an amplitude of a temporal change in the total hemoglobin concentration and an amplitude of a temporal change in one or both of the oxygenated hemoglobin concentration and the deoxygenated hemoglobin concentration as the first indicator. The compression position evaluation unit or the step of calculating may calculate a difference between a phase of the temporal change in the oxygenated hemoglobin concentration and a phase of the temporal change in the deoxygenated hemoglobin concentration as the second indicator. In this manner, by performing evaluation based on the amplitude ratio and the phase difference, it is possible to easily evaluate whether the compression position on the sternum is appropriate.

The measuring unit may obtain a pulse wave component of the total hemoglobin concentration, a pulse wave component of the oxygenated hemoglobin concentration, and a pulse wave component of the deoxygenated hemoglobin concentration by applying filtering process on the numerical values to extract a component that varies due to repetition of the chest compression. The compression position evaluation unit may calculate the first indicator and the second indicator by using the pulse wave component of the total hemoglobin concentration, the pulse wave component of the oxygenated hemoglobin concentration, and the pulse wave component of the deoxygenated hemoglobin concentration, which are obtained by the measuring unit. The step of obtaining may obtain a pulse wave component of the total hemoglobin concentration, a pulse wave component of the oxygenated hemoglobin concentration, and a pulse wave component of the deoxygenated hemoglobin concentration by applying filtering process on the numerical values to extract a component that varies due to repetition of the chest compression. The step of calculating may calculate the first indicator and the second indicator by using the pulse wave component of the total hemoglobin concentration, the pulse wave component of the oxygenated hemoglobin concentration, and the pulse wave component of the deoxygenated hemoglobin concentration, which are obtained in the step of obtaining. In these cases, it is possible to accurately calculate the first indicator and the second indicator based on only the variation component caused by the repetition of the chest compression.

A time from when the measuring unit starts obtaining of the numerical values to when the compression position evaluation unit determines the compression position based on the obtained numerical values may be 5 seconds or more and 30 seconds or less. A time from the start of obtaining the numerical values in the step of obtaining to the determination in the step of determining based on the obtained numerical values may be 5 seconds or more and 30 seconds or less. By securing 5 seconds or more as this time, the determination accuracy can be improved. By setting this time to 30 seconds or less, it is possible to determine the compression position sufficiently earlier than the change cycle of the rescuer (for example, 2 minutes).

Specific examples of an apparatus and a method for evaluating chest compression of the present disclosure will be described below with reference to the drawings. In the following description, the same reference numerals will be applied to the same elements in description of the drawings, and redundant description thereof will be omitted.

Figure 1:
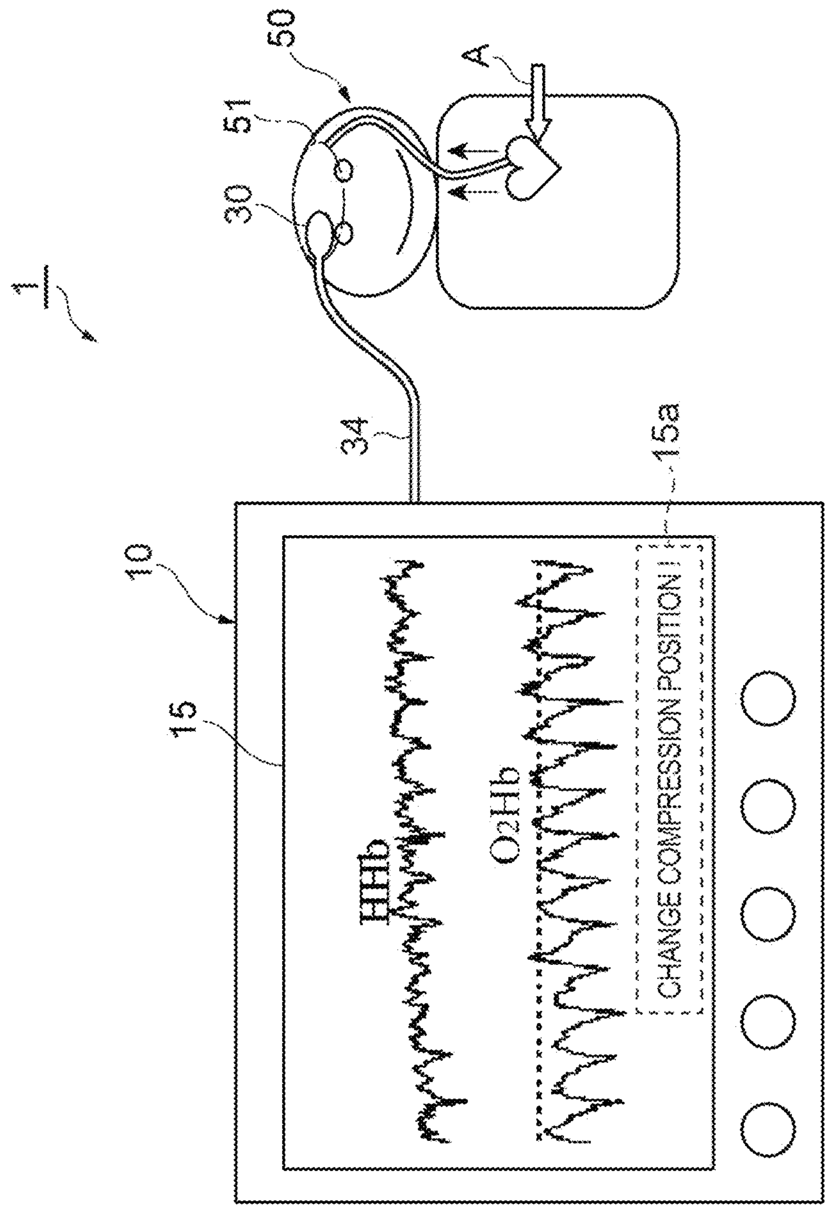
FIG. 1 is a conceptual diagram of an evaluation apparatus according to an embodiment.

FIG. 1 is a conceptual diagram of an evaluation apparatus 1 according to an embodiment. A total hemoglobin concentration (cHb), an oxygenated hemoglobin concentration ($O_2Hb$), and a deoxygenated hemoglobin concentration (HHb) of a head 51 vary due to repetition of chest compression (arrow A in the figure) on the cardiorespiratory arrest person 50. The evaluation apparatus 1 continuously measures temporal changes from initial amounts, that is, relative change amounts, in the total hemoglobin concentration (cHb), the oxygenated hemoglobin concentration ($O_2Hb$), and the deoxygenated hemoglobin concentration (HHb) of the head 51. The evaluation apparatus 1 displays the measurement result on the display unit 15. In addition, the evaluation apparatus 1 calculates a first indicator and a second indicator from temporal changes in relative change amounts in the cHb concentration, the $O_2Hb$ concentration, and the HHb concentration. The evaluation apparatus 1 evaluates whether the compression position on the sternum is appropriate based on the first indicator and the second indicator. In a case where the compression position is inappropriate, the evaluation apparatus 1 displays an element 15*a* on the display unit 15, the element 15*a* indicating an instruction to change the compression position, to notify the rescuer that the compression position is inappropriate.

The evaluation apparatus 1 makes measurement lights having a plurality of wavelengths incident on a predetermined light incident position from a probe 30 fixed to the surface of the head 51. The evaluation apparatus 1 detects intensities of the measurement lights emitted from the predetermined light detection position on the surface of the head 51 to examine the magnitude of attenuation by $O_2Hb$ and HHb at each wavelength. The evaluation apparatus 1 calculates temporal relative change amounts of cHb, $O_2Hb$, and HHb based on the magnitude of attenuation at each wavelength. The evaluation apparatus 1 repeats the incidence of the measurement lights, the detection of the intensities of the measurement lights, and the calculation of the temporal relative change amounts of cHb, $O_2Hb$, and HHb. The evaluation apparatus 1 performs filtering process on the time-series data, which is the calculation result, to remove low-frequency components, thereby extracting a short-cycle time variation component (a pulse wave component) caused by repetition of chest compression. The wavelengths of the measurement lights are included in the near infrared region and include three wavelengths such as 735 nm, 810 nm, and 850 nm in one example.

Figure 2:
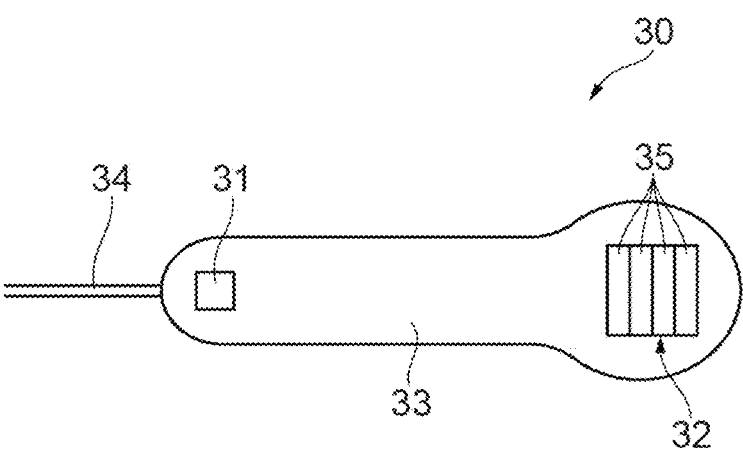
FIG. 2 is a plan view schematically showing a configuration of a probe.

FIG. 2 is a plan view schematically showing the configuration of the probe 30. The probe 30 is fixed to, for example, the forehead without hair or the vicinity of the carotid artery by an adhesive tape, an elastic band, or the like. The probe 30 includes a light incidence portion 31 and a light detection portion 32. The light incidence portion 31 and the light detection portion 32 are arranged at an interval of, for example, 5 cm from each other, and are substantially integrated by a flexible black silicon rubber holder 33. The interval between the light incidence portion 31 and the light detection portion 32 may be substantially within a range of 3 cm to 4 cm or may be equal to or greater than 4 cm. The material of the holder 33 may be replaced with another material having flexibility equivalent to that of silicon rubber. The probe 30 is electrically connected to a main body unit 10 (see FIG. 1) of the evaluation apparatus 1 via a cable 34.

The light incidence portion 31 receives a control signal transmitted from the main body unit 10 and outputs the measurement lights. The measurement lights are pulsed light and enter the cortical layer on the surface of the head 51 substantially perpendicularly. The light incidence portion 31 includes a semiconductor light emitting element such as a laser diode (LD), a light emitting diode (LED), or a super luminescent diode (SLD), and a circuit for driving the light emitting element. The light emitting element and the driving circuit may be provided in the main body unit 10. In that case, the probe 30 and the main body unit 10 are connected via an optical fiber, and the light incidence portion 31 includes a distal end portion of the optical fiber.

The light detection portion 32 generates detection signals corresponding to the intensities of the measurement lights that have propagated through the head 51 and emitted from the surface of the head 51. The light detection portion 32 includes a plurality of photodetectors 35 arranged in a distance direction from the light incidence portion 31. The plurality of photodetectors 35 are arranged side by side along an arrangement direction of the light incidence portion 31 and the light detection portion 32. Distances from the light incidence portion 31 to photodetectors 35 are different for each photodetector 35.

Each photodetector 35 generates the electrical detection signals corresponding to the intensities of the received measurement lights. Each photodetector 35 includes a semiconductor light receiving element such as a photodiode (PD) or an avalanche photodiode (APD) and a preamplifier that integrates and amplifies a current output from the semiconductor light receiving element. Thus, the photodetector 35 can detect weak measurement light with high sensitivity to generate the detection signals, and transmit the detection signals to the main body unit 10 via the cable 34. The light detection portion 32 may be a one-dimensional or twodimensional optical sensor, and may be configured by, for example, a CCD image sensor or a CMOS image sensor.

Figure 3:
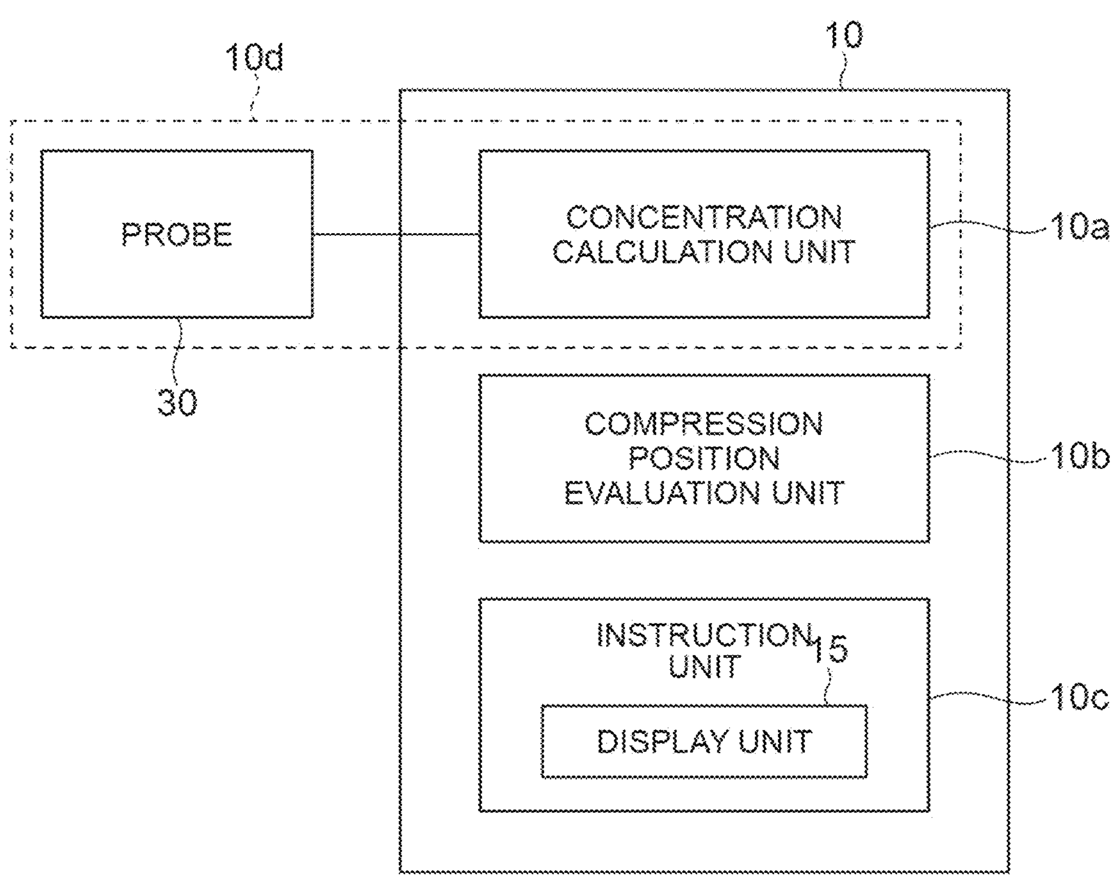
FIG. 3 is a block diagram illustrating a functional configuration example of a main body unit.

As shown in FIG. 1, the evaluation apparatus 1 includes the main body unit 10 in addition to the probe 30 described above. FIG. 3 is a block diagram illustrating a functional configuration example of the main body unit 10. The main body unit 10 includes a concentration calculation portion 10*a*, a compression position evaluation unit 10*b*, and an instruction unit 10*c*. The concentration calculation portion 10*a* is a calculation portion in the present embodiment, and constitutes a measuring unit 10*d* together with the light incidence portion 31 and the light detection portion 32 described above. The measuring unit 10*d* obtains numerical values relating to temporal changes from initial amounts, in the cHb concentration, the $O_2$Hb concentration, and the HHb concentration in the head 51 of the cardiorespiratory arrest person 50. The compression position evaluation unit 10*b* determines whether the compression position on the sternum is appropriate based on the first indicator and the second indicator. The first indicator is relating to a temporal change ratio of the $O_2$Hb concentration or/and the HHb concentration with respect to the temporal change in the cHb concentration. The second indicator is relating to a correlation between the temporal change in the $O_2$Hb concentration and the temporal change in the HHb concentration. The instruction unit 10*c* includes the display unit 15 described above, and instructs the rescuer to change the compression position in a case where the compression position on the sternum is inappropriate.

Figure 4:
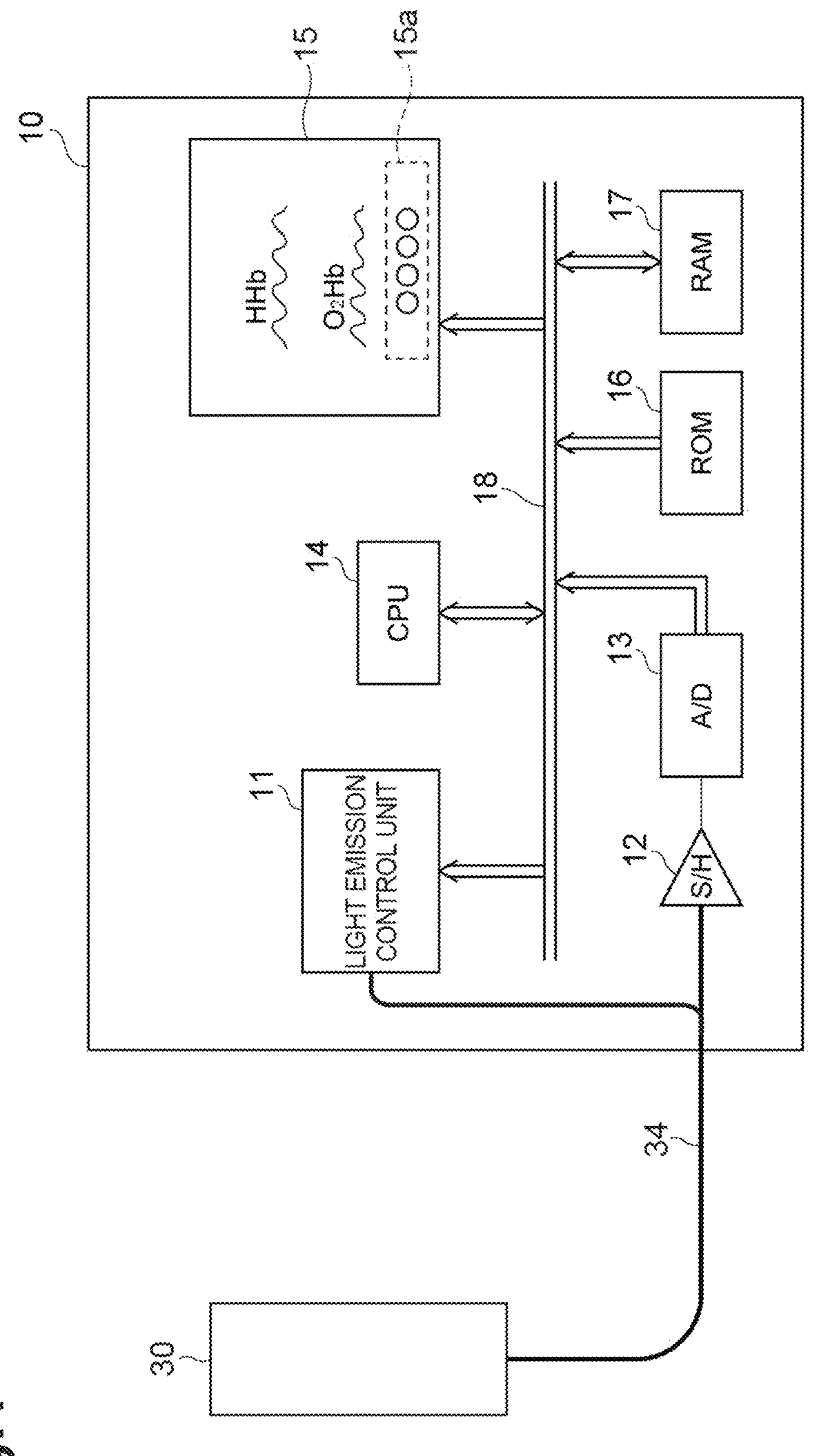
FIG. 4 is a diagram illustrating an example of a hardware configuration of the main body unit.

FIG. 4 is a diagram illustrating a hardware configuration example of the main body unit 10. The main body unit 10 includes a light emission control unit 11, a sample and hold circuit 12, an A/D conversion circuit 13, a CPU 14, the display unit 15, a ROM 16, a RAM 17, and a data bus 18.

The light emission control unit 11 is constituted by a circuit that controls the light incidence portion 31 of the probe 30. The light emission control unit 11 is electrically connected to the data bus 18. The light emission control unit 11 receives a control signal for controlling the light incidence portion 31 from the CPU 14 electrically connected to the data bus 18. The control signal includes information such as intensities and wavelengths of the measurement lights output from the light incidence portion 31. The light emission control unit 11 controls the light incidence portion 31 based on the control signal received from the CPU 14. The light incidence portion 31 outputs measurement lights corresponding to the control signal.

The sample and hold circuit 12 receives detection signals transmitted from the probe 30 via the cable 34 and holds the detection signals. The A/D conversion circuit 13 converts the detection signals into digital signals and outputs the digital signals to the CPU 14. The sample and hold circuit 12 simultaneously holds values of the detection signals corresponding to the number of the photodetectors 35. The sample and hold circuit 12 is electrically connected to the data bus 18. The sample and hold circuit 12 receives sample signals indicating timings for holding the detection signals from the CPU 14 via the data bus 18. Upon receiving the sample signals, the sample and hold circuit 12 simultaneously holds a plurality of the detection signals input from the plurality of photodetectors 35 of the probe 30. The sample and hold circuit 12 is electrically connected to the A/D conversion circuit 13, and outputs each of the plurality of held detection signals to the A/D conversion circuit 13.

The A/D conversion circuit 13 converts the detection signals from analog signals to digital signals. The A/D conversion circuit 13 sequentially converts the plurality of detection signals received from the sample and hold circuit 12 into digital signals. The A/D conversion circuit 13 is electrically connected to the data bus 18, and outputs the converted detection signals to the CPU 14 via the data bus 18.

The CPU 14 realizes various functions by reading and executing a program stored in the ROM 16. As one of the functions, the CPU 14 calculates, based on the detection signals received from the A/D conversion circuit 13, numerical values relating to temporal changes from initial amounts in the $O_2$Hb concentration and the HHb concentration of the head 51, and a numerical value relating to a temporal change from an initial amount in the total hemoglobin concentration (cHb) which is a sum of the $O_2$Hb concentration and the HHb concentration. Further, the CPU 14 applies filtering process on the temporal change in the $O_2$Hb concentration, the HHb concentration, and the cHb concentration, and removes frequency components less than a predetermined frequency from frequency components included in the these temporal changes. As a result, a temporal variation component (a pulse wave component) caused by the repetition of chest compression is extracted. After performing such a process, the CPU 14 sends the result to the display unit 15 via the data bus 18. The concentration calculation portion 10*a* shown in FIG. 3 comprises the sample hold circuit 12, the A/D conversion circuit 13, and the CPU 14. A method of calculating the temporal changes in the $O_2$Hb concentration, the HHb concentration, and the cHb concentration based on the detection signals, and a method of filtering will be described later.

FIGS. 5 and 6 are diagrams conceptually showing the temporal changes from initial amounts in the $O_2$Hb concentration and the HHb concentration. The horizontal direction represents time, and the vertical direction represents concentration. Curve G11 represents the temporal change from the initial amount in the $O_2$Hb concentration. Curve G12 represents the temporal change from the initial amount in the HHb concentration. Part (a) of FIG. 5 shows a case where an amplitude $A_{O2Hb}$ of the temporal change from the initial amount in the $O_2$Hb concentration is higher than an amplitude $A_{HHb}$ of the temporal change from the initial amount in the HHb concentration ($A_{O2Hb}/A_{HHb}>1$) is shown. This case is equivalent to a case where a ratio of the amplitude $A_{O2Hb}$ of the temporal change from the initial amount in the $O_2$Hb concentration to an amplitude $A_{cHb}$ of the temporal change from the initial amount in the cHb concentration is more than 0.5 ($A_{O2Hb}/A_{cHb}>0.5$). Further, this case is equivalent to a case where a ratio of the amplitude $A_{HHb}$ of the temporal change from the initial amount in the HHb concentration to the amplitude $A_{cHb}$ of the temporal change from the initial amount in the cHb concentration is less than 0.5 ($A_{HHb}/A_{cHb}<0.5$). Conversely, part (b) of FIG. 5 shows a case where the amplitude $A_{HHb}$ are higher than the amplitude $A_{O2Hb}$ ($A_{O2Hb}/A_{HHb}<1$). This case is equivalent to a case where the ratio of the amplitudes $A_{O2Hb}$ to the amplitudes $A_{cHb}$ is less than 0.5 ($A_{O2Hb}/A_{cHb}<0.5$). Further, this case is equivalent to a case where the ratio of the amplitude $A_{HHb}$ of the temporal change from the initial amount in the HHb concentration to the amplitude $A_{cHb}$ of the temporal change from the initial amount in the cHb concentration is higher than 0.5 ($A_{HHb}/A_{cHb}>0.5$). Part (a) of FIG. 6 shows a case where an absolute value of a phase difference e between the temporal change from the initial amount in the $O_2$Hb concentration and the temporal change from the initial amount in the HHb concentration are low, and part (b) of FIG. 6 shows a case where the absolute value of the phase difference φ is high.

As shown in an example described later, in a case where the amplitude $A_{O2Hb}$ is higher than a predetermined ratio with respect to the amplitude $A_{HHb}$, that is, the amplitude $A_{O2Hb}$ is higher than a predetermined ratio with respect to the amplitude $A_{cHb}$ (part (a) of FIG. 5) and the absolute value of the phase difference φ is less than a certain value (part (a) of FIG. 6), the compression position on the sternum is appropriate and TOI gradually increases. On the other hand, in a case where the amplitude $A_{O2Hb}$ is less than the predetermined ratio with respect to the amplitude $A_{HHb}$, that is, the amplitude $A_{O2Hb}$ is less than the predetermined ratio with respect to the amplitude $A_{cHb}$ (part (b) of FIG. 5) and the absolute value of the phase difference e is higher than the certain value (part (b) of FIG. 6), the compression position on the sternum is not appropriate, and TOI becomes leveling off or gradually decreases. Therefore, the CPU 14 calculates the first indicator relating to the ratio ($A_{O2Hb}/A_{HHb}$) between the amplitudes $A_{O2Hb}$ and $A_{HHb}$, and calculates the second indicator relating to the phase difference φ. The first indicator may be the amplitude ratio ($A_{O2Hb}/A_{HHb}$) itself, or may be another numerical value (for example, the ratio of time integral values) correlated with the amplitude ratio ($A_{O2Hb}/A_{HHb}$). The first indicator may be a time-moving mean value of the amplitude ratio ($A_{O2Hb}/A_{HHb}$) or the another numerical value, or may be another value similar to a mean value. The second indicator may be the phase difference e itself or an absolute value thereof itself, or may be another numerical value (for example, a peak time difference) correlated with the phase difference e or the absolute value thereof. The second indicator may be a time-moving mean value of the phase difference e or the absolute value thereof or the another numerical value, or may be another value similar to a mean value.

From the above-described equivalent relationship, the first indicator may be the amplitude ratio ($A_{O2Hb}/A_{cHb}$) itself, or may be another numerical value (for example, a ratio of time integral values) having a correlation with the amplitude ratio ($A_{O2Hb}/A_{cHb}$). The first indicator may be a time-moving mean value of the amplitude ratio ($A_{O2Hb}/A_{cHb}$) or the another numerical value, or may be another value similar to a mean value. Further, the first indicator may be the amplitude ratio ($A_{HHb}/A_{cHb}$) itself, or may be another numerical value (for example, a ratio of time integral values) having a correlation with the amplitude ratio ($A_{HHb}/A_{cHb}$). The first indicator may be a time-moving mean value of the amplitude ratio ($A_{HHb}/A_{cHb}$) or the another numerical value, or may be another value similar to a mean value.

The compression position evaluation unit 10*b* shown in FIG. 3 is configured by the CPU 14. That is, the CPU 14 determines whether the compression position on the sternum is appropriate based on the first indicator and the second indicator described above. For example, in a case where the first indicator indicates that the amplitude ratio ($A_{O2Hb}/A_{HHb}$ or $A_{O2Hb}/A_{cHb}$) is less than a first threshold value and the second indicator indicates that the absolute value of the phase difference φ converted to $R^2$ is less than a second threshold value, the CPU 14 determines that the compression position on the sternum is inappropriate. The first threshold value is, for example, 0.5 or more and 1.0 or less in terms of $SnO_2$. In one example, the first threshold value is 1. The CPU 14 may determine that the compression position on the sternum is inappropriate in a case where the first indicator indicates that the amplitude ratio ($A_{HHb}/A_{cHb}$) is higher than a first threshold value and the second indicator indicates that the absolute value of the phase difference p converted into $R^2$ is less than the second threshold value. In a case where the first threshold value is 1, the CPU 14 determines that the compression position is inappropriate when the amplitude $A_{O2Hb}$ is less than the amplitude $A_{HHb}$. The second threshold value is, for example, 0 or more and 0.7 or less in terms of $R^2$ Reference is again made to FIG. 4. The display unit 15 is electrically connected to the data bus 18, and visually displays calculation results relating to temporal changes from initial amounts in the $O_2Hb$ concentration and the HHb concentration transmitted from the CPU 14 via the data bus 18. Furthermore, in a the case where the CPU 14 determines that the compression position on the sternum is inappropriate, the display unit 15 displays the element 15*a*. The element 15*a* is a character, a figure, a symbol, a picture, or the like, or a combination thereof for instructing the rescuer to change the compression position. The evaluation apparatus 1 may include a speaker that outputs a voice and/or a warning sound for instructing the rescuer to change the compression position instead of or together with the display on the display unit 15 for instructing the rescuer to change the compression position. The instruction unit 10*c* illustrated in FIG. 3 includes the CPU 14 and one or both of the display unit 15 and the speaker.

In the present embodiment, "instruct to change the compression position" means prompting the rescuer to change the compression position. The instruction to change the compression position conceptually includes an active instruction that explicitly instructs that the compression position should be changed and a passive instruction that conveys that the compression position is inappropriate. As a system of instructing the change of the compression position, various systems by which the rescuer can recognize the necessity of changing the compression position can be applied.

Figure 7:
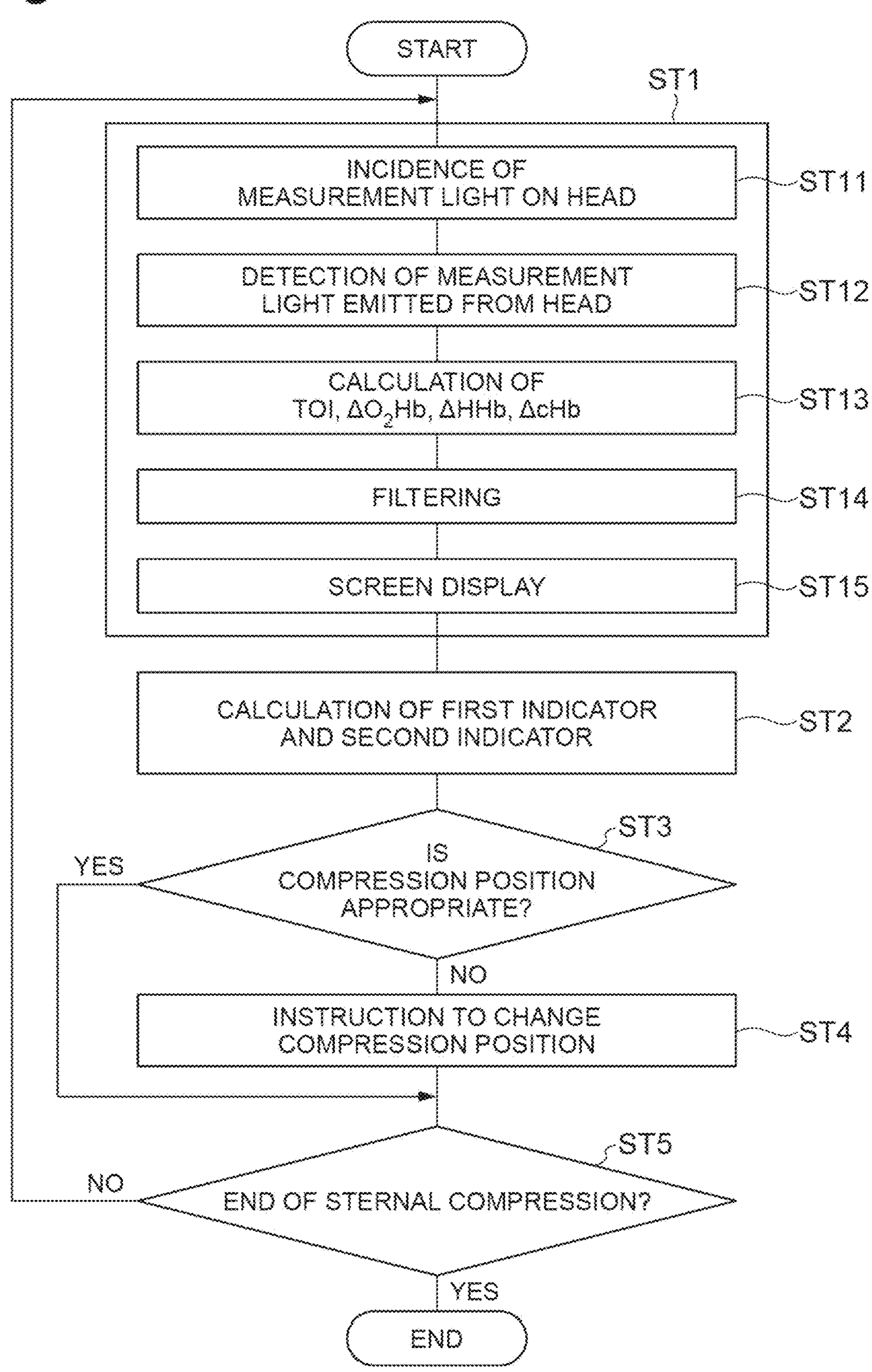
FIG. 7 is a flowchart illustrating an evaluation method according to an embodiment.

Next, an operation of the evaluation apparatus 1 will be described. In addition, an evaluation method according to the present embodiment will be described. FIG. 7 is a flowchart showing an evaluation method according to the present embodiment. In the following description, a case where three measurement lights having wavelengths $\lambda_1$ to $\lambda_3$ are used will be described as an example.

First, the light emission control unit 11 sequentially outputs measurement lights having wavelengths $\lambda_1$ to $\lambda_3$ from the light incidence portion 31 based on an instruction signal from the CPU 14. These measurement lights enter the head 51 from the light incident position (light incidence step ST11). The measurement lights incident on the head 51 are scattered in the head 51 and propagates while being absorbed by the component to be measured, and a part thereof reaches the light detection position of the head 51. The measurement lights having reached the light detection position are emitted from the head 51 and detected by the plurality of photodetectors 35 (light detection step ST12). Each photodetector 35 generates the detection signals corresponding to the intensities of the detected measurement lights. These detection signals are sent to and held by the sample and hold circuit 12 of the main body unit 10, and then converted into digital signals by the A/D conversion circuit 13.

Part (a) of FIG. 8 is a diagram illustrating the incident timings of the measurement lights having wavelengths $\lambda_1$ to $\lambda_3$. Part (b) of FIG. 8 is a diagram illustrating the output timings of the digital signals from the A/D conversion circuit 13. As shown in FIG. 8, when the measurement light having wavelength $\lambda_1$ is made incident, N (N is the number of photodetectors 35) digital signals $D_1(1)$ to $D_1(N)$ respectively corresponding to the N photodetectors 35 are sequentially output from the A/D conversion circuit 13. Subsequently, when the measurement light having wavelength $\lambda_2$ is made incident, N digital signals $D_2(1)$ to $D_2(N)$ respectively corresponding to the N photodetectors 35 are sequentially output from the A/D conversion circuit 13. Subsequently, when the measurement light having wavelength $\lambda_3$ is made incident, N digital signals $D_3(1)$ to $D_3(N)$ respectively corresponding to the N photodetectors 35 are sequentially output from the A/D conversion circuit 13.

Subsequently, the CPU 14 calculates TOI based on the digital signals $D_1(1)$ to $D_1(N)$, $D_2(1)$ to $D_2(N)$, and $D_3(1)$ to $D_3(N)$. The CPU 14 uses at least one of the digital signals $D_1(1)$ to $D_1(N)$, at least one of the digital signals $D_2(1)$ to $D_2(N)$, and at least one of the digital signals $D_3(1)$ to $D_3(N)$ to obtain a numerical value relating to the temporal change amount in the $O_2Hb$ concentration from the initial value ($\Delta O_2Hb$), a numerical value relating to the temporal change amount in the HHb concentration from the initial value ($\Delta$HHb), and a numerical value relating to the temporal change amount in the total hemoglobin concentration from the initial value ($\Delta$cHb) (calculation step ST13). The CPU 14 removes frequency components lower than a predetermined frequency among frequency components included in these change amounts ($\Delta$cHb, $\Delta$O2Hb, $\Delta$HHb) by filtering process, and extracts pulse wave components of the respective change amounts (filtering process step ST14). These change amounts ($\Delta$cHb, $\Delta O_2Hb$, $\Delta$HHb) after the filtering process are displayed on the display unit 15 (display step ST15). The light incidence step ST11, the light detection step ST12, the calculation step ST13, the filtering process step ST14, and the display step ST15 described above are included in the measurement step ST1 for obtaining the numerical values relating to $\Delta$cHb, $\Delta O_2Hb$, and $\Delta$HHb in the head 51.

CPU 14 calculates the first indicator relating to the ratio of one or both of $\Delta O_2Hb$ and $\Delta$HHb to $\Delta$cHb, and calculates the second indicator relating to the correlation between $\Delta O_2Hb$ and $\Delta$HHb (step ST2). For example, the first indicator is an amplitude ratio of $\Delta O_2Hb$ to $\Delta$cHb, an amplitude ratio of $\Delta$HHb to $\Delta$cHb, or an amplitude ratio of $\Delta O_2Hb$ to $\Delta$HHb, and the second indicator is a phase difference between $\Delta O_2Hb$ and $\Delta$HHb. The CPU 14 determines whether the compression position on the sternum is appropriate based on the first indicator and the second indicator (compression position evaluation step ST3). As described above, for example, the CPU 14 determines that the compression position on the sternum is inappropriate when the first indicator indicates that the amplitude ratio ($A_{O2Hb}/A_{HHb}$) or the amplitude ratio ($A_{O2Hb}/A_{cHb}$) is less than the first threshold value and the second indicator indicates that the absolute value of the phase difference (p converted to $R^2$ is less than the second threshold value.

In a case where the CPU 14 determines that the compression position on the sternum is inappropriate (step ST3: NO), the CPU 14 instructs the display unit 15 to display the element 15*a* for instructing the rescuer to change the compression position (instruction step ST4). Alternatively, in a case where the evaluation apparatus 1 comprises a speaker, the CPU 14 may cause the speaker to output a voice and/or a warning sound for instructing the rescuer to change the compression position. In a case where the CPU 14 determines that the compression position on the sternum is appropriate (step ST3: YES), the instruction step ST4 is not performed.

In the evaluation apparatus 1 and the concentration measuring method according to the present embodiment, the above-described steps ST1 to ST4 are repeated until the chest compression ends (step ST5).

Here, contents of the calculation by CPU 14 in the calculation step ST13 and the filtering process step ST14 will be described in detail.

At a certain light detection position, when the values of the detection signals corresponding to the measurement light wavelengths $\lambda_1$ to $\lambda_3$ at the time $T_0$ are $D_{\lambda1}(T_0)$ to $D_{\lambda3}(T_0)$ and the values at the time $T_1$ are $D_{\lambda1}(T_1)$ to $D_{\lambda3}(T_1)$, change amounts of detected light intensities at a time $T_0$ to $T_1$ is expressed by following formulas (1) to (3).

[Formula 1]

$$\Delta OD_1(T_1) = \log\left(\frac{D_{\lambda1}(T_1)}{D_{\lambda1}(T_0)}\right) \tag{1}$$

[Formula 2]

$$\Delta OD_2(T_1) = \log\left(\frac{D_{\lambda2}(T_1)}{D_{\lambda2}(T_0)}\right) \tag{2}$$

[Formula 3]

$$\Delta OD_3(T_1) = \log\left(\frac{D_{\lambda3}(T_1)}{D_{\lambda3}(T_0)}\right) \tag{3}$$

In the formulas (1) to (3), $\Delta OD_1(T_1)$ is the temporal change amount of the detected light intensity at wavelength $\lambda_1$, $\Delta OD_2(T_1)$ is the temporal change amount of the detected light intensity at wavelength $\lambda_2$, and $\Delta OD_3(T_1)$ is the temporal change amount of the detected light intensity at wavelength λ3.

Temporal relative change amounts of the concentrations of $O_2Hb$ and HHb over time from time $T_0$ to time $T_1$ are denoted by $\Delta O_2Hb(T_1)$ and $\Delta HHb(T_1)$, respectively. $\Delta O_2Hb(T_1)$ and $\Delta HHb(T_1)$ can be obtained by following formula (4).

[Formula 4]

$$\begin{pmatrix} \Delta O_2Hb(T_1) \\ \Delta HHb(T_1) \end{pmatrix} = \begin{pmatrix} a_{11} & a_{12} & a_{13} \\ a_{21} & a_{22} & a_{23} \end{pmatrix} \begin{pmatrix} \Delta OD_1(T_1) \\ \Delta OD_2(T_1) \\ \Delta OD_3(T_1) \end{pmatrix} \tag{4}$$

In the formula (4), coefficients an to $a_{23}$ are constants obtained from the extinction coefficients of $O_2Hb$ and HHb with respect to lights having wavelengths $\lambda_1$, $\lambda_2$, and $\lambda_3$. The temporal relative change amount $\Delta cHb(T_1)$ of cHb in the head 51 can be obtained by following formula (5).

$$\Delta cHb(T_1) = \Delta O_2Hb(T_1) + \Delta HHb(T_1) \quad \text{[Formula 5]}$$

The CPU 14 performs the above-described calculation with respect to one detection signal among the N light detection positions, and calculates temporal relative change amounts ($\Delta O_2Hb$, $\Delta$HHb, $\Delta$cHb) of the $O_2Hb$ concentration, the HHb concentration, and the cHb concentration. Further, the CPU 14 performs, any one of the following filtering processes, for example, on the temporal relative change amounts ($\Delta O_2Hb$, $\Delta$HHb, $\Delta$cHb) calculated in this manner.

(1) Filtering Process by Digital Filter

An data sequence relating to the temporal relative change amounts ($\Delta O_2Hb$, $\Delta$HHb, $\Delta$cHb) obtained in a predetermined cycle is denoted by X(n). N is an integer. A non-cyclic linear phase digital filter is realized by multiplying each data in the the data sequence X(n) by, for example, the following filter coefficient A(n) with n=0 as a temporal center.

$$A(0) = 3/4$$

$$A(3) = A(-3) = -1/6$$

$$A(6) = A(-6) = -1/8$$

$$A(9) = A(-9) = -1/12$$

To explain in more detail, the delay operator of the data sequence X(n) is expressed by following formula (6). F is a temporal frequency (the unit is 1/sec). Ω is an angular frequency, and ω=2πf. T is a cycle at which the data sequence X(n) is obtained, and is set to a cycle of, for example, 1/20 second in order to measure a variation waveform up to about 150 times per minute (2.5 Hz).

[Formula 6]

$$e^{j\omega nt} = \mathrm{COS}(\omega nT) + jSIN(\omega nT)$$
$$e^{-j\omega nt} = \mathrm{COS}(\omega nT) - jSIN(\omega nT) \tag{6}$$

In this case, characteristics of the digital filter when the above-described filter coefficient A(n) is used is described by following formula (7).

[Formula 7]

$$R(\omega) = \frac{3}{4} - \frac{1}{6}\left(e^{-3j\omega T} + e^{+3j\omega T}\right) - \frac{1}{8}\left(e^{-6j\omega T} + e^{+6j\omega T}\right) - \frac{1}{12}\left(e^{-9j\omega T} + e^{+9j\omega T}\right) = \frac{3}{4} - \frac{1}{3}\mathrm{COS}(3\omega T) - \frac{1}{4}\mathrm{COS}(6\omega T) - \frac{1}{6}\mathrm{COS}(9\omega T) \tag{7}$$

In this manner, the digital filter is represented by a product-sum operation of the data sequence X(n) and each corresponding coefficient. When the temporal frequency f in the formula (7) is converted into a temporal frequency F per minute (the unit: 1/min), following formula (8) is obtained.

[Formula 8]

$$R(F) = \frac{3}{4} - \frac{1}{3}\mathrm{COS}\left(\frac{3\pi}{600}F\right) - \frac{1}{4}\mathrm{COS}\left(\frac{6\pi}{600}F\right) - \frac{1}{6}\mathrm{COS}\left(\frac{9\pi}{600}F\right) \tag{8}$$

FIG. 9 is a graph showing this R(F) and shows the filter characteristics of the digital filter. In FIG. 9, the horizontal axis represents the heart rate per minute, and the vertical axis represents the value of R(F). FIG. 10 is a graph showing an example of a result obtained by removing (or reducing) frequency components less than a predetermined frequency from frequency components included in a temporal relative change amount of $O_2Hb$ ($\Delta O_2Hb$) by using the digital filter shown in FIG. 9 to extract a temporal variation component caused by a spontaneous heart beat simulating repetition of chest compression. In FIG. 10, a graph G21 indicates the relative change amount ($\Delta O_2Hb$) before the filtering process, a graph G22 indicates long-period components (frequency components less than the predetermined frequency) included in the relative change amount ($\Delta O_2Hb$) before the filtering process, and a graph G23 indicates the relative change amount ($\Delta O_2Hb$) after the filtering process. As shown in FIG. 10, the temporal variation component (the pulse wave component) caused by repetition of spontaneous heartbeat or chest compression can be suitably extracted by the above-described digital filter.

(2) Filtering Process by Smoothing Operation (Least Square Error Curve Fitting)

With n=0 as the temporal center in the data sequence X(n) described above, the least square error curve fitting using a high-order function (for example, a fourth order function) is performed on the data sequence X(n) obtained during a predetermined period of time (for example, 3 seconds, 5 beats) before and after the temporal center. The constant term of the obtained high-order function is regarded as a smoothed component (frequency component less than the predetermined frequency) at n=0. That is, by subtracting the smoothed frequency component from the original data X(0), it is possible to remove the frequency components less than the predetermined frequency from the frequency components included in the relative change amount to separate and extract the temporal variation component (the pulse wave component) caused by the repetition of the chest compression.

FIG. 11 is a graph showing a result obtained by removing (or reducing) the frequency components less than the predetermined frequency from frequency components included in the temporal relative change amount of cHb (ΔcHb) to extract the temporal variation component (the pulse wave component) caused by the spontaneous heart beat simulating repetition of the chest compression by using such filtering process. In FIG. 11, a graph G31 shows the relative change amount (ΔcHb) before the filtering process, a graph G32 shows long-period components (frequency component less than the predetermined frequency) included in the relative change amount (ΔcHb) before the filtering process, a graph G33 shows the relative change amount (ΔcHb) after the filtering process, and a graph G34 shows a mean amplitude for five seconds of the relative change amount (ΔcHb) after the filtering process. As shown in FIG. 11, it is possible to preferably extract the temporal variation component (the pulse wave component) caused by the repetition of the spontaneous heartbeat or the chest compression by the filtering process by the smoothing operation described above.

(3) Filtering Process for Making the Local Maximum Part and the Local Minimum Part of Variation Constant Parts (a) and (b) of FIG. 12 are diagrams for explaining the concept of the present filtering process. In this filtering process, for example, the local maximum values in the temporal changes of the relative change amounts ($\Delta O_2Hb$, ΔHHb, or ΔcHb) is obtained, and as shown in part (a) of FIG. 12, the local maximum value P1 of the temporal change graph G41 is regarded as a constant value, thereby removing frequency components less than the predetermined frequency included in the relative change amounts ($\Delta O_2Hb$, ΔHHb, or ΔcHb). Alternatively, for example, the local minimum values in the temporal changes of the relative change amounts ($\Delta O_2Hb$, ΔHHb, or ΔcHb) are obtained, and as shown in part (b) of FIG. 12, the local minimum value P2 of the temporal change graph G41 is regarded as a constant value, thereby removing frequency components less than the predetermined frequency included in the relative change amounts ($\Delta O_2Hb$, ΔHHb, or ΔcHb). In this manner, by bringing the local maximum value P1 and/or the local minimum value P2 close to a constant value, it is possible to suitably extract the temporal variation component (the pulse wave component) caused by the repetition of the chest compression.

Effects obtained by the evaluation apparatus 1 and the evaluation method of the present embodiment described above will be described. As is clear from examples described later, the ratio of the temporal change in the $O_2Hb$ concentration and the HHb concentration to the temporal change in the cHb concentration, and the correlation between the temporal change in the $O_2Hb$ concentration and the temporal change in the HHb concentration vary depending on the compression position on the sternum. In addition, there is a significant correlation between both the ratio and the correlation and the tendency (ascending tendency, descending tendency, or leveling off tendency) of the temporal change in TOI of the head 51.

In the evaluation method and the evaluation apparatus 1 of the present embodiment, it is determined whether the compression position on the sternum is appropriate, that is, whether the tendency of the temporal change in TOI of the head 51 is the ascending tendency, the descending tendency, or the leveling off tendency, based on the first indicator relating to the above-mentioned ratio and the second indicator relating to the above-mentioned correlation. And then, in a case where the compression position on the sternum is inappropriate, an instruction to change the compression position is given. In this manner, by evaluating whether the compression position on the sternum is appropriate and notifying the rescuer of the fact that the chest compression position is inappropriate in a case where the chest compression is not appropriately performed, it is possible to bring the tendency of the temporal change in TOI of the head 51 close to an ascending tendency and to increase the success rate of cardiopulmonary resuscitation.

As in the present embodiment, the measuring unit 10*d* may include the light incidence portion 31 that makes the measurement lights incident on the head 51, the light detection portion 32 that detects the measurement lights having propagated through the head 51 and generates the detection signals corresponding to the intensities of the measurement lights, and the concentration calculation portion 10*a* that calculates the numerical values relating to the temporal changes in the cHb concentration, the $O_2Hb$ concentration, and the HHb concentration based on the detection signals. The measurement step ST1 may include the light incidence step ST11 of making the measurement lights incident on the head 51, the light detection step ST12 of detecting the measurement lights having propagated through the head 51 and generating detection signals corresponding to the intensities of the measurement lights, and the calculation step ST13 of calculating the numerical values relating to temporal changes in the cHb concentration, the $O_2Hb$ concentration, and the HHb concentration based on the detection signals. In these cases, temporal changes in the cHb concentration, the $O_2Hb$ concentration, and the HHb concentration of the head 51 can be measured non-invasively and simply. Therefore, it is possible to easily measure the temporal changes in the cHb concentration, the $O_2Hb$ concentration, and the HHb concentration of the head 51 while performing the chest compression.

As in the present embodiment, the compression position evaluation unit 10*b* or the compression position evaluation step ST3 may calculate the ratio ($A_{O2Hb}/A_{cHb}$, $A_{HHb}/A_{cHb}$) of amplitudes of temporal changes of one or both of the $O_2Hb$ concentration and the HHb concentration to an amplitude of the temporal change of the cHb concentration as the first indicator, and calculate phase difference $\varphi$ between the phase of the temporal change of the $O_2Hb$ concentration and the phase of the temporal change of the HHb concentration as the second indicator. In this case as well, by evaluating whether the compression position on the sternum is appropriate, and notifying the rescuer the fact that the compression position is inappropriate in the case where the compression position is inappropriate, it is possible to bring the tendency of the temporal change in TOI of the head 51 close to an ascending tendency to increase the success rate of cardiopulmonary resuscitation.

As in the present embodiment, the compression position evaluation unit 10*b* or the compression position evaluation step ST3 may determine that the compression position on the sternum is inappropriate in the case where the first indicator indicates that the ratio ($A_{O2Hb}/A_{cHb}$) of the amplitude $A_{O2Hb}$ of the temporal change in the $O_2Hb$ concentration to the amplitude $A_{cHb}$ of the temporal change in the cHb concentration is less than the first threshold value and where the second indicator indicates that the absolute value, which is a value in terms of $R^2$, of the phase difference $\varphi$ between the temporal change in $O_2Hb$ concentration and the temporal change in HHb concentration are less than the second threshold. For example, in this manner, by comparing the magnitude between the amplitude ratio and the first threshold value and comparing the magnitude between the absolute value of the phase difference and the second threshold, it is possible to easily evaluate whether the compression position on the sternum is appropriate.

As in the present embodiment, the first threshold value may be 0.5 or more and 1.0 or less in terms of $SnO_2$. For example, in this case, it is possible to more accurately evaluate whether the compression position on the sternum is appropriate.

As in the present embodiment, the second threshold value may be 0 or more and 0.7 or less in terms of $R^2$. For example, in this case, it is possible to more accurately evaluate whether the compression position on the sternum is appropriate.

As in the present embodiment, the concentration calculation portion 10*a* may obtain the pulse wave component of the cHb concentration, the pulse wave component of the $O_2Hb$ concentration, and the pulse wave component of the HHb concentration by performing filtering process on the numerical values to extract the component that vary due to the repetition of chest compression. The compression position evaluation unit 10*b* may calculate the first indicator and the second indicator using the pulse wave component of the cHb concentration, the pulse wave component of the $O_2Hb$ concentration, and the pulse wave component of the HHb concentration. The measurement step ST1 may include the step ST14 of performing filtering process on the numerical values to extract components that vary due to the repetition of chest compression to obtain the pulse wave component of the cHb concentration, the pulse wave component of the $O_2Hb$ concentration, and the pulse wave component of the HHb concentration. The step ST2 may calculate the first indicator and the second indicator using the pulse wave component of the cHb concentration, the pulse wave components of the $O_2Hb$ concentration, and the pulse wave components of the HHb concentration. In these cases, it is possible to accurately calculate the first indicator and the second indicator based on only the variation component (the pulse wave component) caused by the repetition of the chest compression.

In the evaluating method and the evaluation apparatus 1 of the present embodiment, $SnO_2$ may be calculated as the first indicator relating to the temporal change ratio of the $O_2Hb$ concentration with respect to the temporal change in the cHb concentration, and $R^2$ may be calculated as the second indicator relating to the correlation between the temporal change in the $O_2Hb$ concentration and the temporal change in the HHb concentration. Then, based on $SnO_2$ and $R^2$, it may be determined whether the compression position on the sternum is appropriate, that is, whether the tendency of the temporal change in TOI of the head 51 is ascending tendency, descending tendency or leveling off tendency. In the case where the compression position on the sternum is inappropriate, a change in the compression position is indicated. In this manner, by evaluating whether the compression position on the sternum is appropriate and notifying the rescuer that the compression position is inappropriate when the compression position is inappropriate, it is possible to bring the tendency of the temporal change in TOI of the head 51 close to ascending tendency and increase the success rate of cardiopulmonary resuscitation.

The $SnO_2$ can be obtained from a linear regression between a numerical value relating to the pulse wave component of the cHb concentration and a numerical value relating to the pulse wave component of the $O_2Hb$ concentration, which are obtained in a predetermined period (for example, up to 5 seconds retroactively from the calculation timing). The $SnO_2$ is a slope (regression coefficient) of a regression line obtained by performing linear regression using a numerical value relating to the pulse wave component of the cHb concentration obtained in the predetermined period as an explanatory variable and a numerical value relating to the pulse wave component of the $O_2Hb$ concentration obtained in the predetermined period as an objective variable. The $R^2$ can be obtained from a linear regression between a numerical value relating to the pulse wave component of the $O_2Hb$ concentration and a numerical value relating to the pulse wave component of the HHb concentration, which are obtained in a predetermined period (for example, up to 5 seconds retroactively from present time). The $R^2$ is a determination coefficient obtained by performing linear regression using a numerical value relating to the pulse wave component of the $O_2Hb$ concentration obtained in the predetermined period as an explanatory variable and a numerical value relating to the pulse wave component of the HHb concentration obtained in the predetermined period as an objective variable. As described later, the changes in $SnO_2$ and $R^2$ have correlations with TOI of the head 51.

Even in a case where the first indicator and the second indicator are calculated using mean values such as moving averages of the numerical values, it is preferable that the time from when the measuring unit 10*d* or the measurement step ST1 starts obtaining the numerical values to when the compression position evaluation unit 10*b* or the compression position evaluation step ST3 determines the compression position based on the obtained numerical values is 5 seconds or more and 30 seconds or less. By securing 5 seconds or more as the time, it is possible to sufficiently secure the number of numerical values used for calculation of mean values or the like and regression calculation to improve determination accuracy. By setting this time to 30 seconds or less, it is possible to prompt the change of the compression position sufficiently earlier than the change cycle (for example, 2 minutes) of the rescuer.

Example

Next, an example in which temporal changes in TOI, the cHb concentration, the $O_2Hb$ concentration, and the HHb concentration in cardiopulmonary resuscitation were actually observed will be described. In the present example, in order to continue chest compression for a long period of time during cardiopulmonary resuscitation, two rescuers performed chest compression while alternating about every two minutes. When the rescuer changes, the compression position on the sternum will of course change slightly.

Part (a) of FIG. 13 is a graph showing a temporal change in the cHb concentration of the head in the cardiopulmonary resuscitation. Part (b) of FIG. 13 is a graph showing a temporal change in TOI of the head in the cardiopulmonary resuscitation. In these figures, the horizontal axis represents time (hour:minute). The vertical axis of part (a) of FIG. 13 represents a relative value of the cHb concentration, and the vertical axis of part (b) of FIG. 13 represents the magnitude of TOI (unit: %). In the figure, periods A in which one of the two rescuers performs chest compression and periods B in which the other rescuer performs chest compression are shown. In the figure, arrows C indicating the timing at which the pulse check was performed and arrows D indicating the timing at which adrenaline (epinephrine) was administered are shown together.

Each of FIGS. 14 to 17 is a graph showing temporal changes of (a) change amounts in $O_2Hb$ concentration and HHb concentration, (b) pulse wave oxygen saturation, that is, a slope in linear regression between the pulse wave component of the cHb concentration and the pulse wave component of the $O_2Hb$ concentration (regression coefficient: $SnO_2$), (c) determination coefficient ($R^2$) obtained by linear regression between the pulse wave component of the $O_2Hb$ concentration and the pulse wave component of the HHb concentration, and (d) tissue oxygen saturation (TOI), in each of the parts E1 to E4 of FIG. 13. The horizontal axis of these graphs represent time (hour:minute:second), the unit of the vertical axis of part (a) is arbitrary unit, and the unit of the vertical axes of parts (b) and (d) is %. In part (a), the broken line indicates the change amount of the $O_2Hb$ concentration, and the solid line indicates the change amount of the HHb concentration.

Referring to FIGS. 13 to 17, it can be seen that there are a period in which TOI has ascending tendency, a period in which TOI has descending tendency, and a period in which TOI has leveling off tendency, in a plurality of periods including the period A and the period B. The period in which TOI has ascending tendency is, for example, a period including the part E2, and is illustrated in FIG. 15. The period in which TOI has descending tendency is, for example, a period including the part E3, and is illustrated in FIG. 16. The period in which TOI has leveling off tendency is, for example, a period including the part E1 and a period including the part E4, and is illustrated in FIGS. 14 and 17. Referring to parts (a) and (b) of FIG. 15, it is understood that the value of $SnO_2$ is higher than 50% and the ratio of the pulse wave component of the $O_2Hb$ concentration to the pulse wave component of the cHb concentration is high, in the period in which TOI has ascending tendency. On the other hand, referring to parts (a) and (b) of FIGS. 14, 16, and 17, it can be seen that the value of $SnO_2$ is at least partially less than 50% and the ratio of the pulse wave component of the $O_2Hb$ concentration to the pulse wave component of the cHb concentration is low, in the period in which TOI has descending tendency or leveling off tendency. As shown in part (c) of FIG. 15, in a period in which TOI has ascending tendency, the value of $R^2$ is relatively high, and it can be said that the correlation between the pulse wave component of the $O_2Hb$ concentration and the pulse wave component of the HHb concentration is high. On the other hand, as shown in part (c) of FIGS. 14, 16, and 17, in a period in which TOI has descending tendency or leveling off tendency, the value of $R^2$ is relatively low, and the correlation between $O_2Hb$ pulse wave component and HHb pulse wave component is low.

As described above, there is a significant correlation between the ratio of the pulse wave component of the $O_2Hb$ concentration to the pulse wave component of the cHb concentration and the tendency (ascending tendency, descending tendency, or leveling off tendency) of the temporal change in TOI of the head. There is also a significant correlation between the tendency of the temporal change of TOI of the head and the correlation between the pulse wave component of the $O_2Hb$ concentration and the pulse wave component of the HHb concentration. That is, as the ratio of the pulse wave component of the $O_2Hb$ concentration to the pulse wave component of the cHb concentration is higher and the correlation between the temporal change in the $O_2Hb$ concentration and the temporal change in the HHb concentration is lower, the tendency of TOI becomes ascending tendency. On the other hand, as the ratio of the pulse wave component of the $O_2Hb$ concentration to the pulse wave component of the cHb concentration is lower and the correlation between the temporal change in the $O_2Hb$ concentration and the temporal change in the HHb concentration is higher, the tendency of TOI becomes leveling off tendency or descending tendency. Even in a case where the ratio of the temporal change in the $O_2Hb$ concentration to the temporal change in the cHb concentration is low, when the ratio is higher than a predetermined ratio, there is a possibility that the TOI becomes ascending tendency.

Since the cHb concentration is the sum of the $O_2Hb$ concentration and the HHb concentration, it is estimated from the above results that there is a significant correlation between the ratio of the pulse wave component of the HHb concentration to the pulse wave component of the cHb concentration and the tendency (ascending tendency, descending tendency, or leveling off tendency) of the temporal change of TOI of the head. That is, as the ratio of the pulse wave component of the HHb concentration to the pulse wave component of the cHb concentration is lower, TOI becomes ascending tendency. On the other hand, as the ratio of the pulse wave component of the HHb concentration to the pulse wave component of the cHb concentration is higher, TOI becomes leveling off tendency or descending tendency. Even in a case where the ratio of the temporal change in the HHb concentration to the temporal change in the cHb concentration is high, when the ratio is less than a predetermined ratio, there is a possibility that the TOI becomes ascending tendency.

Among a plurality of periods in which the same rescuer performs chest compression, there are a period in which TOI has ascending tendency and a period in which TOI has descending tendency or leveling off tendency. Therefore, it can be said that such a difference in the tendency of the temporal change in TOI is not caused by the individual difference of the chest compression technique. As discussed above, when the rescuers change, the compression position on the sternum of course changes slightly. Therefore, it is considered that such a difference in the tendency of the temporal change in TOI is caused by a change in the compression position on the sternum at the time of alternation. That is, it is possible to suitably determine whether the compression position on the sternum is appropriate based on the ratio of the pulse wave component of the $O_2Hb$ concentration or/and the HHb concentration to the pulse wave component of the cHb concentration and the correlation between the temporal change in the $O_2Hb$ concentration and the temporal change in the HHb concentration. The above example shows that even if the chest compression is performed at an appropriate cycle and power, TOI of the head is not improved unless the compression position is appropriate.

The evaluation apparatus and evaluation method for chest compression according to the present disclosure are not limited to the embodiments described above, and various other modifications are possible. For example, in the above embodiment, near-infrared spectroscopy is exemplified as a method of measuring temporal changes in the cHb concentration, the $O_2Hb$ concentration, and the HHb concentration. The method of measuring temporal changes in the cHb concentration, the $O_2Hb$ concentration, and the HHb concentration is not limited to this, and various other methods can be used.

In the above-described embodiment, the instruction to change the compression position is given to the rescuer. The target to be instructed is not limited to the rescuer. For example, in a case where the chest compression is performed mechanically and automatically, an instruction signal for changing the position of the arm that compresses the sternum may be output from the instruction unit of the evaluation apparatus to the device that performs the chest compression.

INDUSTRIAL APPLICABILITY

The embodiment can be used as an apparatus and a method capable of increasing the success rate of cardiopulmonary resuscitation by evaluating whether the chest compression is appropriately performed and notifying a rescuer of the fact that the chest compression is inappropriate in a case where the chest compression is not appropriately performed.

REFERENCE SIGNS LIST

1: evaluation apparatus, 10: main body unit, 10*a*: concentration calculation portion, 10*b*: compression position evaluation unit, 10*c*: instruction unit, 10*d*: measuring unit, 11: light emission control unit, 14: CPU, 15: display unit, 15*a*: element, 16: ROM, 17: RAM, 18: data bus, 30: probe, 31: light incidence portion, 32: light detection portion, 33: holder, 34: cable, 35: photodetector, 50: cardiorespiratory arrest person, 51: head, $A_{HHb}$: amplitude, $A_{O2Hb}$: amplitude, A, B: period, P1: local maximum value, P2: local minimum value, ST1: measurement step, ST3: compression position evaluation step, ST4: instruction step, ST11: light incidence step, ST12: light detection step, ST13: calculation step, ST14: filtering process step, ST15: display step, $\varphi$: phase difference.

The invention claimed is:

1. An evaluation apparatus for chest compression, comprising:

a measuring unit configured to obtain numerical values relating to temporal changes in a total hemoglobin concentration, an oxygenated hemoglobin concentration, and a deoxygenated hemoglobin concentration in a head, which vary due to repetition of the chest compression;

a compression position evaluation unit configured to calculate a first indicator and a second indicator based on the numerical values and determine whether a compression position on a sternum is appropriate based on the first indicator and the second indicator, the first indicator relating to a temporal change ratio of one or both of the oxygenated hemoglobin concentration and the deoxygenated hemoglobin concentration with respect to a temporal change in the total hemoglobin concentration, and the second indicator relating to a correlation between a temporal change in the oxygenated hemoglobin concentration and a temporal change in the deoxygenated hemoglobin concentration; and an instruction unit configured to instruct to change the compression position in a case where the compression position on the sternum is inappropriate, wherein the measuring unit includes:

a light incidence portion configured to make measurement light incident on the head;

a light detection portion configured to detect the measurement light that has propagated through the head and generate a detection signal corresponding to an intensity of the measurement light; and a calculation portion configured to calculate the numerical values based on the detection signal.

2. The evaluation apparatus according to claim 1, wherein the compression position evaluation unit is configured to perform first linear regression based on the numerical values by using a numerical value relating to a pulse wave component of the total hemoglobin concentration as an explanatory variable and a numerical value relating to a pulse wave component of the oxygenated hemoglobin concentration as an objective variable, use a regression coefficient value obtained by the first linear regression as the first indicator, perform second linear regression, based on the numerical values, between the numerical value relating to a pulse wave component of the oxygenated hemoglobin concentration and a numerical value relating to a pulse wave component of the deoxygenated hemoglobin concentration, and use a determination coefficient value obtained by the second linear regression as the second indicator.

3. The evaluation apparatus according to claim 2, wherein the compression position evaluation unit is configured to perform the first linear regression and the second linear regression based on the numerical values obtained during a period from a time of calculation of the first linear regression and the second linear regression to at least 5 seconds before the time of calculation.

4. The evaluation apparatus according to claim 2, wherein the compression position evaluation unit determines that the compression position on the sternum is inappropriate in a case where the regression coefficient value served as the first indicator is less than a first threshold value and the determination coefficient value served as the second indicator is less than a second threshold value.

5. The evaluation apparatus according to claim 4, wherein the first threshold value is 0.5 or more and 1.0 or less.

6. The evaluation apparatus according to claim 4, wherein the second threshold value is 0 or more and 0.7 or less.

7. The evaluation apparatus according to claim 1, wherein the compression position evaluation unit is configured to calculate a ratio, based on the numerical values, between an amplitude of the temporal change in the total hemoglobin concentration and an amplitude of the temporal change in one or both of the oxygenated hemoglobin concentration and the deoxygenated hemoglobin concentration as the first indicator, and calculate a difference between a phase of the temporal change in the oxygenated hemoglobin concentration and a phase of the temporal change in the deoxygenated hemoglobin concentration as the second indicator.

8. The evaluation apparatus according to claim 1, wherein the measuring unit is configured to obtain a pulse wave component of the total hemoglobin concentration, a pulse wave component of the oxygenated hemoglobin concentration, and a pulse wave component of the deoxygenated hemoglobin concentration by applying filtering process on the numerical values to extract a component that varies due to repetition of the chest compression, and wherein the compression position evaluation unit is configured to calculate the first indicator using the pulse wave component of the total hemoglobin concentration and one or both of the pulse wave component of the oxygenated hemoglobin concentration and the pulse wave component of the deoxygenated hemoglobin concentration, which are obtained by the measuring unit, and calculate the second indicator using the pulse wave component of the oxygenated hemoglobin concentration and the pulse wave component of the deoxygenated hemoglobin concentration, which are obtained by the measuring unit.

9. An evaluation method for chest compression, comprising:

obtaining numerical values relating to temporal changes in a total hemoglobin concentration, an oxygenated hemoglobin concentration, and a deoxygenated hemoglobin concentration in a head, which vary due to repetition of the chest compression;

calculating a first indicator and a second indicator based on the numerical values, the first indicator relating to a temporal change ratio of one or both of the oxygenated hemoglobin concentration and the deoxygenated hemoglobin concentration with respect to a temporal change in the total hemoglobin concentration, and the second indicator relating to a correlation between a temporal change in the oxygenated hemoglobin concentration and a temporal change in the deoxygenated hemoglobin concentration;

determining whether a compression position on a sternum is appropriate based on the first indicator and the second indicator;

instructing to change the compression position in a case where the compression position on the sternum is inappropriate, wherein the obtaining includes:

making measurement light incident on the head;

detecting the measurement light that has propagated through the head and generating a detection signal corresponding to an intensity of the measurement light; and calculating the numerical values based on the detection signal.

10. The evaluation method according to claim 9, wherein in the calculating, a first linear regression is performed based on the numerical values by using a numerical value relating to a pulse wave component of the total hemoglobin concentration as an explanatory variable and a numerical value relating to a pulse wave component of the oxygenated hemoglobin concentration as an objective variable, a regression coefficient value obtained by the first linear regression is used as the first indicator, a second linear regression is performed, based on the numerical values, between the numerical value relating to a pulse wave component of the oxygenated hemoglobin concentration and a numerical value relating to a pulse wave component of the deoxygenated hemoglobin concentration, and a determination coefficient value obtained by the second linear regression is used as the second indicator.

11. The evaluation method according to claim 10, wherein in the calculating, the first linear regression and the second linear regression are performed based on the numerical values obtained during a period from a time of calculation of the first linear regression and the second linear regression to at least 5 seconds before the time of calculation.

12. The evaluation method according to claim 10, wherein in the determining, it is determined that the compression position on the sternum is inappropriate when the regression coefficient value served as the first indicator is less than a first threshold value and the determination coefficient value served as the second indicator is less than a second threshold value.

13. The evaluation method according to claim 12, wherein the first threshold value is 0.5 or more and 1.0 or less.

14. The evaluation method according to claim 9, wherein in the obtaining, a pulse wave component of the total hemoglobin concentration, a pulse wave component of the oxygenated hemoglobin concentration, and a pulse wave component of the deoxygenated hemoglobin concentration are obtained by applying filtering process on the numerical values to extract a component that varies due to repetition of the chest compression, and wherein in the calculating, the first indicator is calculated by using the pulse wave component of the total hemoglobin concentration and one or both of the pulse wave component of the oxygenated hemoglobin concentration and the pulse wave component of the deoxygenated hemoglobin concentration, which are obtained in the obtaining, and the second indicator is calculated by using the pulse wave component of the oxygenated hemoglobin concentration and the pulse wave component of the deoxygenated hemoglobin concentration, which are obtained in the obtaining.

15. The evaluation method according to claim 12, wherein the second threshold value is 0 or more and 0.7 or less.

16. The evaluation method according to claim 9, wherein in the calculating, a ratio is calculated as the first indicator, the ratio being between an amplitude of the temporal change in the total hemoglobin concentration and an amplitude of the temporal change in one or both of the oxygenated hemoglobin concentration and the deoxygenated hemoglobin concentration, and a difference is calculated as the second indicator, the difference being between a phase of the temporal change in the oxygenated hemoglobin concentration and a phase of the temporal change in the deoxygenated hemoglobin concentration, based on the numerical values.

* * * * *